United States Patent

Mochly-Rosen et al.

Patent Number: 5,783,405
Date of Patent: Jul. 21, 1998

[54] RAPID SCREENING METHOD FOR EFFECTORS OF SIGNAL TRANSDUCTION

[75] Inventors: Daria Mochly-Rosen, Menlo Park; Dorit Ron, San Francisco; Lawrence M. Kauvar, San Francisco; Eugene W. Napolitano, San Francisco, all of Calif.

[73] Assignee: Terrapin Technologies, Inc., San Francisco, Calif.

[21] Appl. No.: 541,964

[22] Filed: Oct. 10, 1995

Related U.S. Application Data

[63] Continuation-in-part of Ser. No. 487,072, Jun. 7, 1995, Ser. No. 477,346, Jun. 7, 1995, Ser. No. 473,089, Jun. 7, 1995, and a continuation-in-part of Ser. No. 190,802, Feb. 1, 1994, Pat. No. 5,519,003.

[51] Int. Cl.$^6$ ............... C12Q 1/48; C12Q 1/68
[52] U.S. Cl. ............... 435/15; 435/6; 435/7.8
[58] Field of Search ............... 435/6, 7.8, 15

[56] References Cited

U.S. PATENT DOCUMENTS 5,283,173 2/1994 Fields et al. ............... 435/6
5,352,660 10/1994 Pawson ............... 514/12

FOREIGN PATENT DOCUMENTS

WO95/21252 1/1995 WIPO .

OTHER PUBLICATIONS

Derwent Publications Ltd., AN 94–026226 (1994).
Dalrymple, M.A. et al., "The Product of the PRP4 Gene of S. cerevisiae Shows Homology to β Subunits of G Proteins," *Cell* 58: 811–812 (1989).
Dynlacht, B.D. et al., "The dTAF..80 subunit of Drosphila TFIID contains β–transducin repeats," *Nature* 363: 176–179 (1993).
Fong, H.K.W. et al., "Repetitive segmental structure of the transducin β subunit: Homology with the CDC4 gene and identification of related mRNAs," *Proc. Natl. Acad. Sci. USA* 83: 2162–2166 (1986).

Guillemot, F. et al., "Physical linkage of a guanine nulceotide–binding protein–related gene to the chicken major histocompatibility complex," *Proc. Natl. Acad. Sci. USA* 86: 4594–4598 (1989).

Keleher, C.A. et al., "Ssn6–Tup 1 Is a General Repressor of Transcription in Yeast," *Cell* 68: 709–719 (1992).

Mochly–Rosen, D. et al., "Identification of intracellular receptor proteins for activated protein kinase C," *Proc. Natl Acad. Sci. USA* 88:3997–4000 (1991).

Mochly–Rosen, D. et al., "Intracellular Receptors for Activated Protein Kinase C," *J. Biol. Chem* 266(23):14866–14868 (1991).

Peitsch, M.C. et al., "Sequence similarity of phospholipase A2 activating protein and the G protein β–subunits: a new concept of effector protein activation in signal transduction?," *TIBS* 18(8): 292–293 (1993).

Ron, D. et al. "An Autoregulatory Region in Protein Kinase C: The Pseudoanchoring Site" *Proc. Natl. Acad. Sci. USA* 92:492–496 (1995).

Ron, D. et al. "Agonists and Antagonists of Protein Kinase C Function, Derived from its Binding Proteins" *J. Biol. Chem.* 269:21395–21398 (1994).

Ron, D. et al. "Cloning of an Intracellular Receptor for Protein Kinase C: A Homolog of the Beta Subunit of G Proteins" *Proc. Natl. Acad. Sci. USA* 91:839–843 (1994).

(List continued on next page.)

*Primary Examiner*—Eric Grimes
*Attorney, Agent, or Firm*—Morrison & Foerster LLP

[57] ABSTRACT

Methods for assessing libraries of candidate modulators of intracellular signaling transmission pathways are described. The methods assess the ability of candidates from the library to inhibit the binding of peptides which represent participants in the signaling pathways as either a signal-generating protein or its cognate partner binding at a noncatalytic site. Specific peptides useful in this regard have been identified.

12 Claims, 5 Drawing Sheets

OTHER PUBLICATIONS

Ruggieri, R., et al. "MSI1, a Negative Regulator of the RAs–cAMP Pathway in Saccharomyces Cerevisiae" *Proc. Natl. Acad. Sci. USA* 86:8778–8782 (1989).

Smith, B.L. and Mochly–Rosen, D., "Inhibition of Protein Kinase C Function by Injection of Intracellular Receptors for the Enzyme," *Biochem. Biophys. Res. Comm.* 188(3):1235–1240 (1992).

Takagaki, Y. and Manley, J.L., "A Human Polyadenylation Factor Is a G Protein β–subunit Homologue," *J. Biol. Chem* 267(33):23471–23474 (1992).

Tamaki, M. et al. "Rat Lipocortin I cDNA" *Nucleic Acids Res.* 15:7637 (1987).

van der Voorn, L. and Ploegh, H.L. "The WD–40 repeat," *FEBS Lett.* 307(2):131–134 (1992).

Wallner, B., et al. "Cloning and Expression of Human Lipocortin, a Phospholipase A2 Inhibitor with Potential Anti–Inflammatory Activity" *Nature* 320:77–81 (1986).

Weinstat–Saslow et al., "A Transducin–like Gene Maps to the Autosomal Dominant Polycystic Kidney Disease Gene Region" *Genomics* 18:709–711 (1993).

Williams, F.E. and Trumbly, R.J., "Characterization of TUP1, a Mediator of Glucose Repression in *Saccharomyces cerevisiae*," *Mol. Cell. Biol.* 10(12):6500–6511 (1990).

Williams, F.E. et al., "The CYC8 and TUP1 Proteins Involved in Glucose Repression in *Saccharomyces cerevisiae Are Associated in a Protein Complex*," *Mol. Cell. Biol.* 11(6):3307–3316 (1991).

RAPID SCREENING METHOD FOR EFFECTORS OF SIGNAL TRANSDUCTION

This application is a continuation-in-part of U.S. Ser. Nos. 08/473,089, 08/477,346, and 08/487,072, all filed 7 Jun. 1995 and all of which claim priority from PCT Application WO 95/21252 published 10 Aug. 1995. The present application is also a continuation-in-part of U.S. Ser. No. 08/190,802 filed 1 Feb. 1994, now U.S. Pat. No. 5,519,003. The contents of all of the foregoing applications are incorporated herein by reference.

TECHNICAL FIELD

The invention relates to intracellular signal transduction. More specifically, it concerns methods to identify modulators of intracellular signal transduction by assessing the ability of candidate modulators to affect the interaction between a catalytically active signal-generating protein and a cognate binding protein involved in modulating the signal transduction function. The invention also concerns specific embodiments of such methods and the components thereof.

BACKGROUND ART

PCT Application WO 95/21252 described above, discloses and claims peptide compositions which alter the activity of a signal-generating protein with respect to its cognate protein wherein the cognate protein contains at least one WD-40 region which putatively interacts with the signal-generating protein. The peptide compositions mimic the WD-40 regions, thus competing with the interaction of the cognate with the signal-generating protein. This competition results either in inhibiting the signal-generation or activating it.

One specifically exemplified signal-generating protein is protein kinase C (PKC); the illustrated cognate receptor for activated kinase C (RACK), in this case specific for βPKC, was designated RACK1. The gene encoding RACK1 was cloned and sequenced, showing that RACK1 contains the requisite WD-40 regions.

The above PCT application and parent applications herein further describe methods to identify additional pairs of signal-generating proteins and their cognates and methods for recognizing WD-40 sequences in the cognates. These applications also note that such interactions can be used as a system to identify additional molecules that bind the signal-generating protein by measuring the effect of candidate binding molecules on the interaction between the signal-generating protein and either its cognate per se or the polypeptide compositions that mimic the WD-40 regions of the cognate.

In the present invention, several specific peptides have been identified that bind either to the signal-generating protein or to the cognate protein in a signal-affecting manner. The use of the signal-generating protein/cognate system to assay for modulators of signal transduction in assays which are independent of the purity of these participants is described. The PKC enzyme system is illustrated as a specific embodiment. In addition, peptides which reside on the signal-generating protein, as well as those which reside on the cognate or mimics thereof, can be used to modulate the signal-generating interactions.

DISCLOSURE OF THE INVENTION

The present invention is directed to an efficient assay system to identify modulators of intracellular signaling pathways. Because the method takes advantage of inherent biological specificity, it can be conducted on impure preparations of the participants in the signal pathway—the signal-generating protein and its cognate receptor controlling the signal pathway. The assay is conducted by assessing the interaction between the signal-generating protein and its cognate either by measuring binding directly or by measuring a physiological or metabolic effect. The measurement is made in the presence and in the absence of a candidate modulator. Successful candidates which agonize the signal effect an increase in a metabolic or physiological output; antagonists effect a decrease. Both antagonists and agonists compete for binding between cognate and signal-generating protein.

Among successful candidates will be peptides which mimic regions on either the signal-generating protein or the cognate as well as nonpeptide small molecules. Due to their ease of identification, these peptides are particularly useful in alternate forms of the screening assays that detect binding between the peptide and the signal-generating or cognate protein. Although the assay methods disclosed may not all be suitable for direct screening of large chemical libraries, they do enable a sophisticated screening of candidates that can be combined with other techniques for selecting leads.

The methods described herein may involve peptides derived from the cognate or signal-generating protein. By "derived from" we mean that such peptides are either found in the cognate or signal-generating protein, or are modified by a limited number of conservative changes. Preferably the conservative changes represent less than about 20%, more preferably less than about 10%, and most preferably less than about 5% of the residues in the identified native sequence. One way to identify a suitable peptide is to compare sequences among species as is described in Example 4.

The invention is also directed to methods to screen libraries of candidate modulators using the above-described methods and to peptides representative of sites on the signal-generating protein and cognate which are themselves useful in these assays as well as in other applications involving the relevant interaction.

MODES OF CARRYING OUT THE INVENTION

The invention is, perhaps, best understood as a generalization of an illustrative interacting signal-generating pair, wherein the signal-generating protein is PKC and the cognate is an appropriate RACK. A peptide that mimics a PKC binding element contained in the RACK or in the PKC or that mimics a RACK-binding element contained in the PKC can be used as a component of assays relevant to the signal pathway.

PKCs represent a family of signal-generating isoenzymes, at least several of which are present in each cell type. Upon activation by a suitable agent, typically phosphatidylserine (PS) and diacylglycerol (DAG), and in some cases calcium ion, a PKC is translocated subcellularly, generally from the soluble fraction to another location in the cell that is associated with the particulate fraction. Each isoenzyme in this family apparently has a cognate anchoring protein at the appropriate location associated with the physiological or metabolic effect of the activation of each particular isoenzyme. Thus, for example, one or a subset of PKCs contained in cardiac myocytes, when activated, results in a slowing of the contraction rate.

One or a subset of PKCs contained in *Xenopus oocytes*, when activated, effect maturation of the egg. One or a subset of PKCs, when inhibited at the catalytic site, blocks T-lymphocyte activation. See, Birdchall et al. (1994) *J. Pharm. Expt'l Ther.* 268:922. The interaction of a particular PKC isoenzyme with its cognate RACK is required for the metabolic or physiological effect; therefore interference with this interaction will modulate that effect. Alternatively, the effect of the modulation may be agonistic if the interaction of the modulator promotes a conformational change in the signal generating partner corresponding to that normally occurring only upon the concurrent binding of activators (e.g., PS or DAG) and cognate protein, or otherwise results in signal activation.

Figure 1:
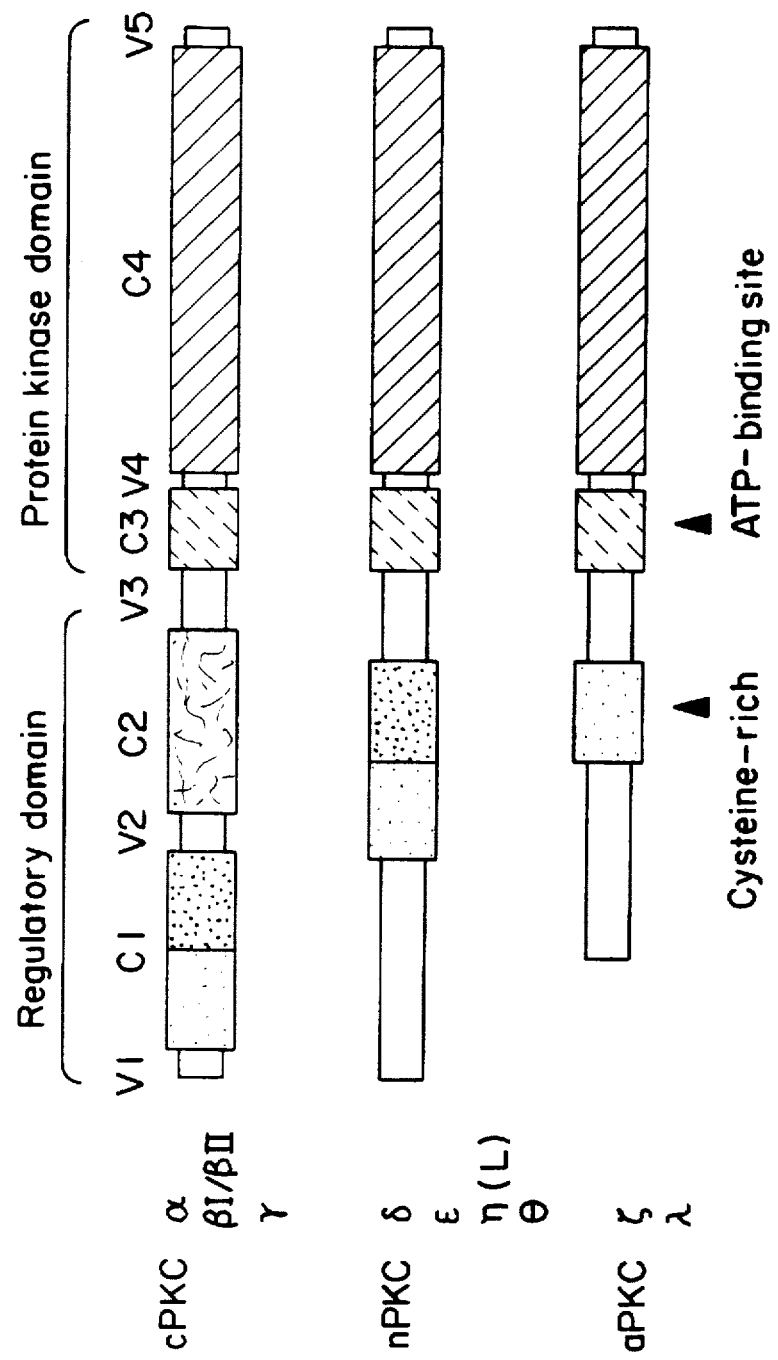
FIG. 1 shows, diagrammatically, the known general primary sequence and domains of various PKC isoenzyme families.

The known PKC isoenzymes can be divided into three major groups as shown in FIG. 1. All of the isoenzymes, regardless of group, contain a protein kinase domain represented by two constant (C) and two variable (V) regions. The regions which are responsible for the enzymatic activity are highly homologous or constant; the C4 region toward the carboxy terminus is thought to contain the catalytic site; the C3 regions upstream are responsible for binding ATP.

Upstream of the protein kinase domain in each case is a regulatory domain. All of the three families, the conventional (cPKC), the novel (nPKC) and atypical (aPKC) contain variable regions at the N-terminus designated V1, and constant regions immediately downstream marked C1. The C1 regions are thought to be involved in activation by phosphatidylserine, diacylglycerol, or pharmacological mimics such as phorbol esters. The C2 region is found only in the cPKC family and is thought to be the site for activation by calcium. However, the picture may not be quite so simple as C1 regions may also be involved in calcium binding, and the atypical class respond poorly to agents such as phorbol esters.

Nevertheless, it now appears clear that sequences is within the regions shown as the regulatory domain are responsible for the interaction of the particular PKC with its cognate RACK. They may also contain a RACK-mimicking region, called a pseudo-RACK site, that prevents binding of PKC to its RACK when the PKC has not been activated. This situation is analogous to the pseudosubstrate sequence which is located elsewhere in the primary sequence and blocks the catalytic site prior to activation of the PKC. It is shown hereinbelow that the relevant regions are specific for the particular isoenzyme involved in a designated signal-generation event.

In the parent applications herein, published as PCT W095/21252, the cognate RACK1 protein which interacts with βPKC (a member of the cPKC family) was cloned and the WD-40 regions putatively responsible for binding to the βPKC were identified through structural analogy. One of these WD-40 peptides was found to induce the kinase activity of PKC in the absence of PKC activators; both this peptide and another representing a WD-40 region rendered the βPKC susceptible to proteolysis, a characteristic of activated PKC forms. All of these peptides were also shown to inhibit the binding of βPKC to RACK1. In principle, the WD-40 regions of the appropriate RACK can serve as antagonists or agonists of the signal generation associated with the corresponding PKC. As described, an assay which shows the effects of members of a library of candidate modulators on interaction between the relevant PKC and its cognate or the relevant PKC and a WD-40 domain derived from said cognate can be used as a screening assay to identify modulators of this signal pathway.

In the illustrative work described below, similar modulation of signal generation is achieved as before by supplying, to a reaction mixture containing PKC, WD-40 peptides derived from the relevant RACK or pseudo-RACK peptides from the PKC regulatory domain which themselves mimic the RACK's binding domains, and examining the effect of a candidate on binding or signal generation. Similarly, the RACK-binding peptides derived from PKC can be used as assay reagents in combination with the appropriate RACK to screen for modulators of the signal-generating pathway by virtue of the ability of the successful candidate to affect the binding of the cognate protein to the signal-generating protein.

Thus, in summary, various counterpart interactions can be tested; in no case are purified components required:

| Component 1 | Component 2 | Assay Method |
| --- | --- | --- |
| Signal-generating protein (e.g. PKC) | Cognate protein (e.g. RACK) | binding, outcome (e.g., translocation) |
| Signal-generating protein (e.g. PKC) | WD-40 region of e.g. a RACK | binding |
| Signal-generating protein (e.g. PKC) | Pseudo-RACK region of PKC | binding |
| RACK-binding region of PKC | Cognate protein, e.g. RACK | binding |
| RACK-binding region of PKC | WD-40 region of RACK | binding |
| RACK-binding region of PKC | Pseudo-RACK region of PKC | binding |

In general, the present invention is directed to screening methods to identify modulators of particular signal pathways. Each assay will involve identifying a cognate protein that binds sufficiently specifically to a catalytically active signal-generating protein, via a noncatalytic site, to permit assay in impure preparations. The interaction of these two components is observed in the presence and absence of a candidate modulator. Depending on the assay system chosen, the interaction and its modification can be observed in a variety of ways, including intracellular binding assays affecting an observable parameter; either a physiological readout, such as change in subcellular distribution, or an artificial construct, such as transcription of a reporter gene, can be used. In no case, however, are purified reagents required, although it may be convenient in some cases, for example, to utilize the peptides identified as illustrated below which represent regions of the signal-generating protein (illustrated by PKC) or its cognate binding protein (represented by the relevant RACK) that are responsible for interaction.

As further described below, the peptides which can be substituted for one or the other component in the assay method are themselves identifiable through conduct of the assay. Thus, the ability of a peptide to affect the interaction of the cognate protein and the signal-generating protein will identify it as a useful component of the assay, as well as a modulator of the signal pathway per se. Once the appropriate peptides are identified, the individual labeled peptides could be used to assess the level of binding. The labeled peptide may represent a region of the signal-generating peptide measured against a composition containing the cognate protein or, conversely, a peptide representing a portion of the cognate protein measured against the composition containing the signal-generating protein. These compositions may be whole cells or cell-free extracts or partially purified extracts.

It will be apparent that when a peptide is chosen as one component of the assay, the screening tests are preferably performed by measuring only binding per se.

Alternatively, both the signal-generating protein and the cognate protein may be contained in a crude preparation and the method for assessing their interaction may include measuring localization of the signal-generating protein within the preparation per se or measuring a metabolic effect of the interaction, such as, for example, maturation of Xenopus oocytes or effect on the contraction rate of cardiac myocytes. The particular method of assessing the interaction will, of course, be appropriate to the partners in the interaction, and can readily be ascertained by taking advantage of the specificity of the signal pathways and their components as illustrated below.

Thus, for convenience, the assays to identify modulating candidate compounds will be described as measuring the effect of the candidate on the "binding" of the counterpart components in the reaction mixture. It will be understood that in the instance where both the cognate protein and the signal-generating protein are the active components of the composition participating in the assay, binding may be measured not only directly, but also by the resulting metabolic or physiological effects.

The examples below illustrate the signal generation specificity in the PKC isoenzyme families. They also illustrate the identification of peptides that may serve as counterpart members of a signal modulation assay.

These examples are intended to illustrate but not to limit the invention.

EXAMPLE 1

Specificity of Negative Chronotropy for εPKC Translocation

Neonatal rat cardiac myocytes were used in this assay. These cells, when prepared in culture, exhibit contractions at approximately the rate of 40–50/15 sec., and it is known that the phorbol ester, 4-β phorbol 12-myristate-13-acetate (PMA) reduces the contraction rate (Johnson, J. A. et al., *Circ Res* (1995) 76:654–653). Previous work has also shown that treating cardiac myocytes with PMA or with norepinephrine (NE) causes translocation of αPKC to the nuclear boundary, βIPKC to the interior of the nuclei, δPKC to the fibrillar and perinuclear structures, and εPKC to cross-striated structures (Disatnik, M.-H. et al., *Exp Cell Res* (1994) 210:287–297). It has also been shown that exogenously added activated PKCs bind similarly (Mochly-Rosen, D. et al., *Molec Biol Cell* (1990) 1:693–706). Since the location to which the various isoenzymes are translocated are different, it has been suggested that the variable regions specific for each isoenzyme (Nishizuka, Y., *Nature* (1988) 334:661–665) should contain at least part of the specific RACK binding site (Disatnik, M.-H. et al., *Exp Cell Res* (1994) 210:287–297). Furthermore, it has been suggested that the V1 region of εPKC determines its substrate specificity (Pears, C. et al., *Biochem J* (1991) 276:257–260).

To show that only translocation of the corresponding isoenzyme is inhibited by one of its fragments—e.g., only translocation of εPKC is inhibited by an εPKC-V1 fragment, cells cultured on chamber slides were permeabilized with saponin (50 μg/ml) in the absence or presence of 100 μg/ml rat recombinant εPKC-V1 or δPKC-V1 fragments containing amino acids 2–144 in each case. Cellular functions, including cell viability, spontaneous and stimulated contraction rates, gene expression and hypertrophy are unaffected by the saponin treatment.

These fragments were prepared by amplifying the relevant portion of the gene from a cDNA library (Stratagene). A FLAG™ epitope (DYKDDDK) (SEQ ID NO:1) was engineered at the 5' end of the fragment and the 0.45 kb PCR fragment was subcloned into pMAL-C2 vector (New England Biolabs) for overexpression as a fusion protein with maltose binding protein in *E. coli*. Protein purification and Factor Xa proteolysis of the fusion proteins was as described by Ron, D. et al., *Proc Natl Acad Sci USA* (1994) 91:839–843.

The intracellular concentration of each fragment was approximately 300 DM or about 3% of the extracellular concentration as determined by quantitative Western blot of washed and extracted cells.

After the εPKC-V1 or δPKC-V1 fragments were administered by permeabilization, the cells were incubated with either 4-α or 4-β PMA. (4α PMA is not active and is used as a control.) The cells were then fixed with methanol and acetone and PKC isoenzyme localization was determined by immunofluorescence; the antisera used to detect δPKC and εPKC do not recognize the administered fragments. Multiple fields of cells for each treatment group and for PKC isoenzymes α, βI, δ, and ε were observed and the data were presented as a percentage of cells having the tested enzyme at the activated site. When the cells were treated with 100 nM PMA for five minutes, it was apparent that neither δPKC-V1 nor εPKC-V1 had any effect on translocation of the α or β isoenzymes whereas each of the δ and ε fragments specifically inhibited the translocation of the corresponding isoenzyme, but not the other isoenzyme. An additional experiment measuring translocation of εPKC at the much lower level of 3 nM PMA also showed complete inhibition by the ε fragment. It has previously been shown that 3 nM PMA is only marginally effective in translocation of PKC isoenzymes other than the ε form (Johnson, J. A. et al., *Circ Res* (1995) 76:654–663).

Figure 2A:
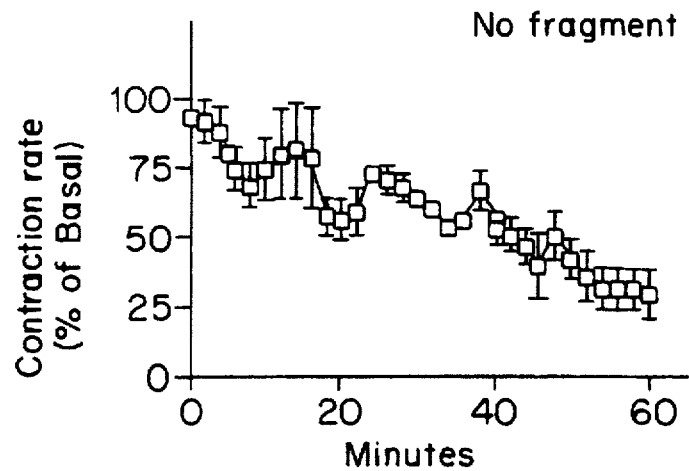
FIG. 2 shows the result of experiments demonstrating that PKC mediated effects on contraction of cardiac myocytes is inhibited by a fragment of the regulatory domain of εPKC but not by a corresponding fragment of δPKC.
Figure 2B:
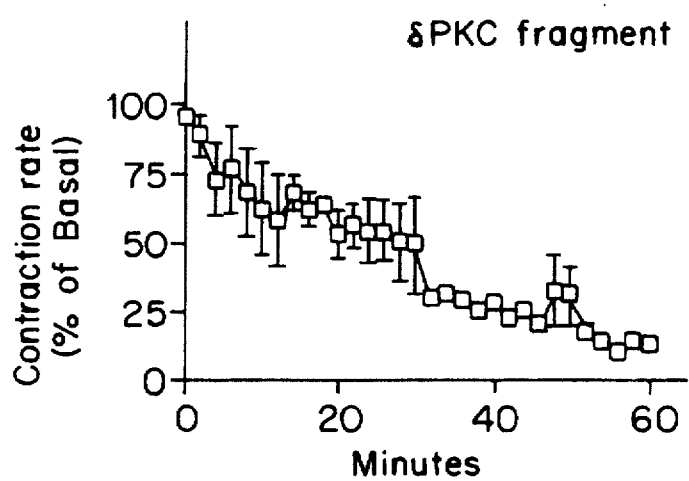
Figure 2C:
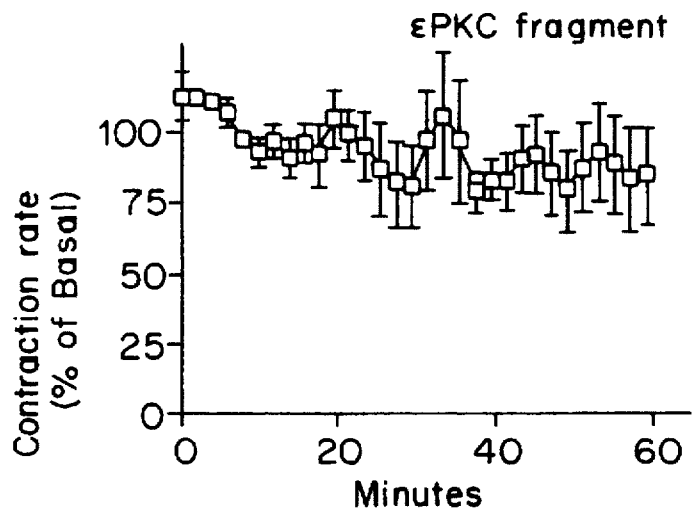

The localization of εPKC to the cross-striated structures suggested that the ε isoenzyme might mediate the effect of PMA on the contraction rate. Cells were cultured and permeabilized with saponin in the presence or absence of 150 μg/ml δ or εPKC-V1 fragments described above. Basal contraction rates were monitored for 10 min, and the cells were then treated with 3 nM PMA. The rate of contraction was monitored over the next 20 minutes. The results are shown in FIG. 2.

As shown, in cells where no fragment was added, the contraction rate is reduced almost to zero within 15 min of the addition of PMA. Similarly, in cells where the δPKC fragment is added, the contraction rate is thus reduced.

However, in cells where the εPKC fragment was added, the contraction rate is maintained. Thus, the εPKC-V1 fragments specifically prevented PMA-induced inhibition of spontaneous contraction. These data, combined with the data described above with respect to translocation and the fact that the εPKC-V1 fragment does not affect the catalytic activity of εPKC in vitro, demonstrate that the translocation of εPKC is an essential step in signaling the chronotropic effect of PMA and that this signaling is inhibited by a fragment containing the V1 region.

The effect of PMA in reducing the contraction rate can be mimicked by controlling the α1 and β1 adrenergic receptors of the myocytes, providing a more physiologically relevant phenomenon. If both the α1 and β1 receptors are activated with NE, an increase in contraction rate occurs; when both receptors are inhibited, NE no longer has this effect. If the α1 receptor is inhibited alone by prazosin, the initial increase in contraction rate is higher; if the β1 receptor alone is inhibited, the contraction rate decreases.

When either the δ or ε fragments described above is substituted for the known inhibitors of the α1 and β1 receptors, the behavior of the cells in response to NE is unaffected by the presence of the δ fragment; however, addition of the ε fragment gives a response similar to that obtained in the presence of prazosin. These data are consistent with the role of the ε fragment in controlling contraction rate since the α1 receptor (inhibited by prazosin) mediates PKC translocation.

Figure 3:
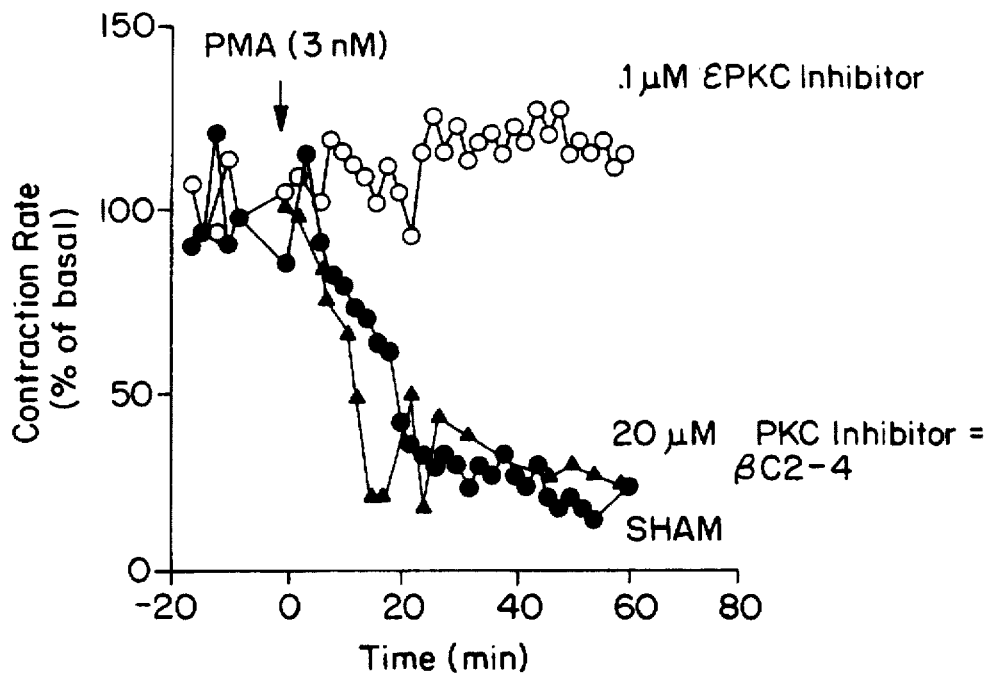
FIG. 3 shows the specific effect of an 8 amino acid peptide derived from the RACK-binding site in the regulatory domain of εPKC on the contraction rate of cardiac myocytes; an analogous peptide from the βPKC has no effect.

FIG. 3 shows the results of a similar experiment using stimulation with 3 nM PMA, and providing peptides of less than 10 residues that block localization of εPKC and βPKC using a 0.1 μM εPKC-derived peptide εV1-2 (sequence EAVSLKPT (SEQ ID NO:2)) or 20 μM of a βPKC-derived peptide βC2-4 (sequence SLNPEWNET (SEQ ID NO:3)). As shown in FIG. 3, stimulation with 3 nM PMA without adding peptides to the permeabilized cells or in the presence of 20 μM of the βPKC localization inhibitor results in negative chronotropy as above.

EXAMPLE 2

Specific Inhibition of βPKC Translocation by C2-Derived Peptides

The parent application herein described binding sites on a particular RACK, RACK1, which are responsible for binding βPKC. It is recognized that if the binding site on PKC is identified, peptides that mimic this binding site could also serve as modulators of βPKC translocation and function. Furthermore, it should be noted that PKC may itself contain pseudo-RACK peptide sequences that mimic the binding sites on RACK and regulate the exposure of the binding site for RACK on PKC. The following experiments do not distinguish between these possibilities; nevertheless, whichever function on the PKC sequence is represented, mimics of the sequence will be effective modulators of the relevant signal pathway.

The cPKC class of isozymes comprises the only members of the PKC general family that contains C2 regions. Other C2-containing proteins such as synaptotagmin and phospholipase Cγ also bind to a mixture of RACKs prepared from cell particulate fractions. It has also been demonstrated that recombinant fragments of synaptotagmin containing the C2 homologous region bind to mixtures of RACKs and inhibit PKC binding to RACKs (Mochly-Rosen, D. et al., *Biochemistry* (1992) 31:8120–8124).

The following experiments demonstrate that certain peptides residing in the C2 region of βPKC are able to inhibit translocation of βPKC and the maturation of *Xenopus* oocytes.

The following βPKC-derived peptides were prepared:
βC2-1 (SEQ ID NO:4): KQKTKTIK (210-217);
βC2-2 (SEQ ID NO:5): MDPNGLSDPYVKL (186-198);
βC2-3 (SEQ ID NO:6): IPDPKSE (201-207);
βC2-4 (SEQ ID NO:3): SLNPEWNET (218-226);
Scrambled βC2-1 (SEQ ID NO:7): TKQKKITK;
Control Peptide (SEQ ID NO:8): LQKAGVDG (266-271).

Recombinantly produced fragments of βPKC were expressed as fusion proteins with GST: Fusion L9 includes the V1 region, the pseudosubstrate sequence, and the C1 and V2 regions (residues 3-182) of βPKC. L10 includes the V1 region, the pseudosubstrate sequence and the first cysteine repeat from the C1 region, as well as the entire C2 and V3 regions (residues 3-76 and 143-339). The numbering is as described in Luo, J.-H. et al., *J Biol Chem* (1993) 248:3715–3719.

Standard overlay assays were performed by blotting RACK1 onto nitrocellulose as described by Mochly-Rosen, D. et al., *Proc Natl Acad Sci USA* (1991) 88:3997–4000. Strips of the nitrocellulose sheet containing 0.1–1 μg RACK1 per strip were incubated in overlay buffer with or without the test fragment added at approximately 10 μM. Addition was in the presence or absence of 50 μg/ml phosphatidyl serine (PS) and 1 mM calcium. The mixture was further incubated for 30 min at room temperature. The strips were then washed and binding of fragment of L9 or L10 to RACK1 was detected with anti-GST polyclonal antibodies followed by labeling with anti-rabbit horseradish peroxidase-linked antibodies and development by addition of substrate.

Using this assay, L10, but not L9 was found to bind RACK1. The PKC activators phosphatidyl serine and calcium did not increase the binding of L10 to RACK1, although these activators are necessary for the binding of intact PKC to RACK1. Thus, these data are consistent with the suggestion that the PKC activators are required to expose the RACK binding site in the intact PKC; this site is already exposed in the C2-containing fragment L10.

To determine whether L10 would inhibit the binding of intact βPKC to RACK1, RACK1 was immobilized on an amylose column and βPKC binding in the presence of PS, DAG and calcium and in the presence of L10 or L9 was determined. In the presence of L10, βPKC binding to RACK1 was completely inhibited; however, this was not true of L9. Similar results were obtained in an overlay assay.

Similar overlay assays were conducted using the above-listed peptides as candidate inhibitors for the binding of L10 to RACK1. The C2-derived peptides βC2-1, βC2-2 and pC2-4 peptides were successful in inhibiting binding of L10 to RACK1; however βC2-3 and scrambled βC2-1 were not.

In addition to the foregoing cell-free assays, the association of βPKC with RACK1 and the ability of peptides derived from the C2 region to interrupt this interaction was tested in rat neonatal cardiac myocytes in culture. The presence of RACK1 in these cells was confirmed by immunostaining. RACK1 was found at perinuclear structures and throughout the cytosol. Treating with NE or PMA did not alter these locations. It was also demonstrated that activated βII PKC, but not C2-less isoenzymes δ or εPKC, colocalized with RACK1.

The C2-derived peptides that had been shown to inhibit βPKC binding to RACK1 in vitro were then tested for their ability to inhibit activation-induced translocation in myocytes.

The myocytes were exposed to 100 nM PMA for 15 min after transient permeabilization with saponin (50 μg/ml) in the presence and absence of the test peptides. 80% of the cells that had not been treated with peptides showed localization of β1 PKC to perinuclear structures. However, when βC2-1, βC2-2 or βC2-4 at 10 μM extracellular concentration had been supplied to the permeabilized cells, translocation of both βI PKC and βII PKC isoenzymes was inhibited by 65–95%. βC2-4 was the most effective. Control peptides described above did not affect translocation.

Consistent with the results in Example 1, treating non-permeabilized cardiac myocytes with 100 nM PMA resulted in translocation of εPKC from the nucleus to the perinuclear and cross-striated structures and of δPKC from the perinuclear and fibrilar cytosolic structures in 80% and 90% of the cells respectively. Permeabilization and treatment of the cells with the C2 peptides derived from βPKC had no effect on the translocation of these C2-less isozymes.

While the chronotropy of myocytes is not affected by βPKC isoenzymes, the insulin-induced maturation of *Xenopus oocytes* is mediated by the β form. Insulin treatment of these oocytes results in translocation of βPKC and maturation is delayed by the PKC-specific catalytic inhibitor pseudosubserate peptide. PKC translocation is blocked by injection of purified RACKs or a peptide corresponding to the PKC binding site on RACKs. (Smith, B. L. et al., *Biochem Biophys Res Commun* (1992) 188:1235–1240; Ron, D. et al., *J Biol Chem* (1994) 269:21395–21398).

Figure 4:
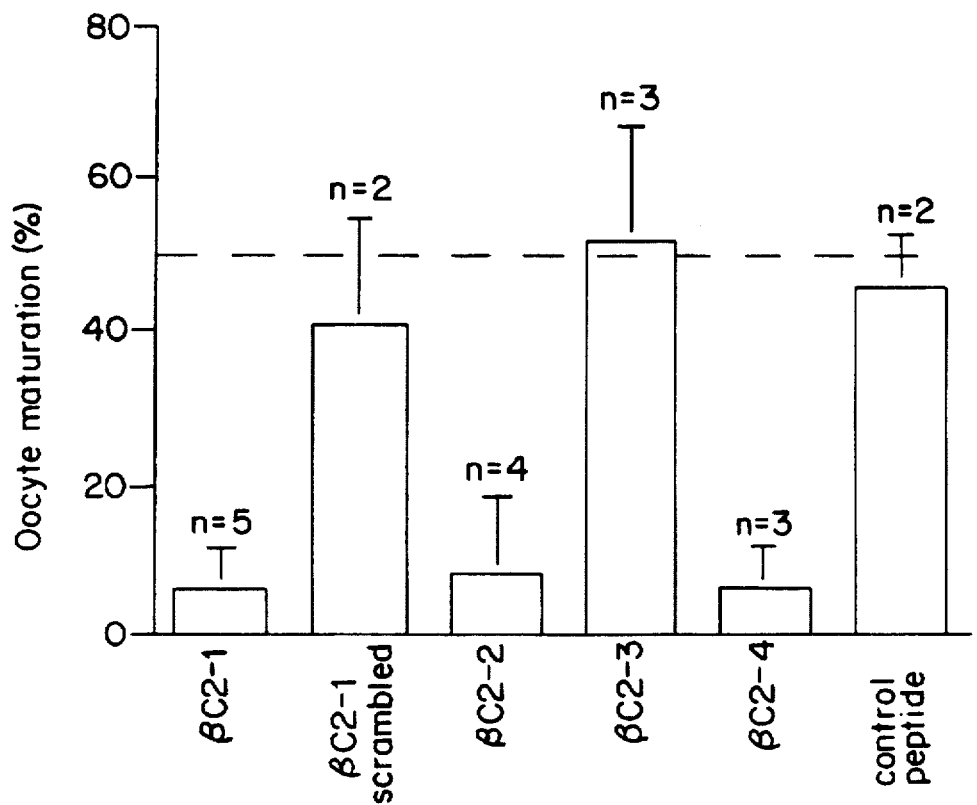
FIG. 4 shows the specific effect of peptides derived from the RACK-binding site of βPKC on maturation of *Xenopus* oocytes.

Accordingly, the maturation of Xenopus oocytes was used as an alternative assay system to test the function of the peptides derived from the C2 region described above. In this assay, oocytes were injected with 50 μM of the test peptide one hour before insulin treatment (8.25 μg/ml). Insulin-induced oocyte maturation was then determined by monitoring the appearance of a white spot in the animal pole of the oocyte that is indicative of germinal vesicle breakdown in maturation. 10–15 oocytes were included per assay and oocytes were scored for 35 hours after treatment. As expected, βC2-1, βC2-2 and βC2-4 supplied in the range of 5 μM–500 μM significantly delayed oocyte maturation in a dose-dependent manner. The control peptides did not. The association of this effect with the prevention of translocation of βPKC to the particulate fraction in *Xenopus oocytes* was confirmed in a separate experiment. The peptide βC2-4 inhibited βPKC translocation but not θPKC in T-Jurkat cells. FIG. 4 shows the effect of these various peptides on *Xenopus oocyte* maturation.

EXAMPLE 3

Agonist Effect of Interacting Peptides

Figure 5A:
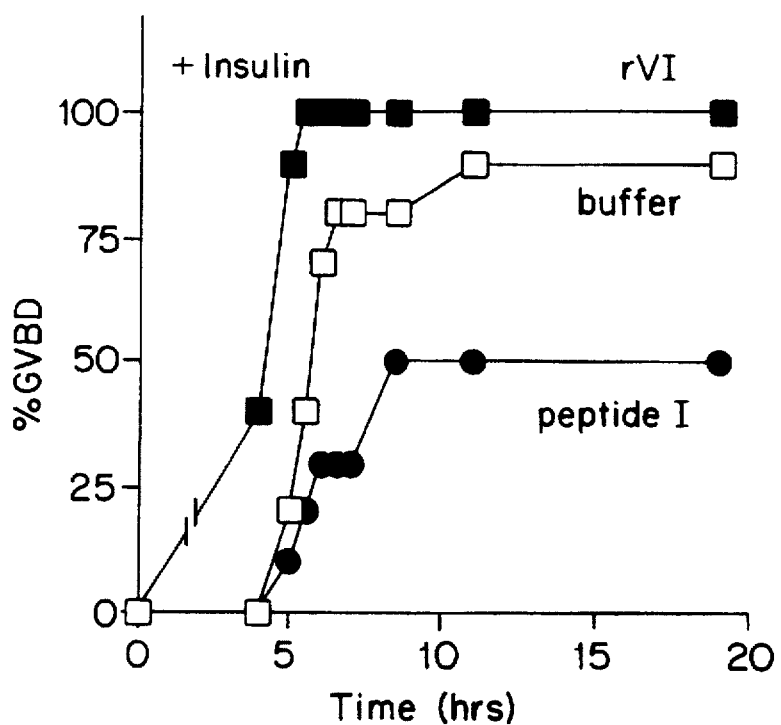
FIG. 5 shows the effects of peptides derived from RACK1 on PKC mediated maturation of *Xenopus* oocytes.
Figure 5B:
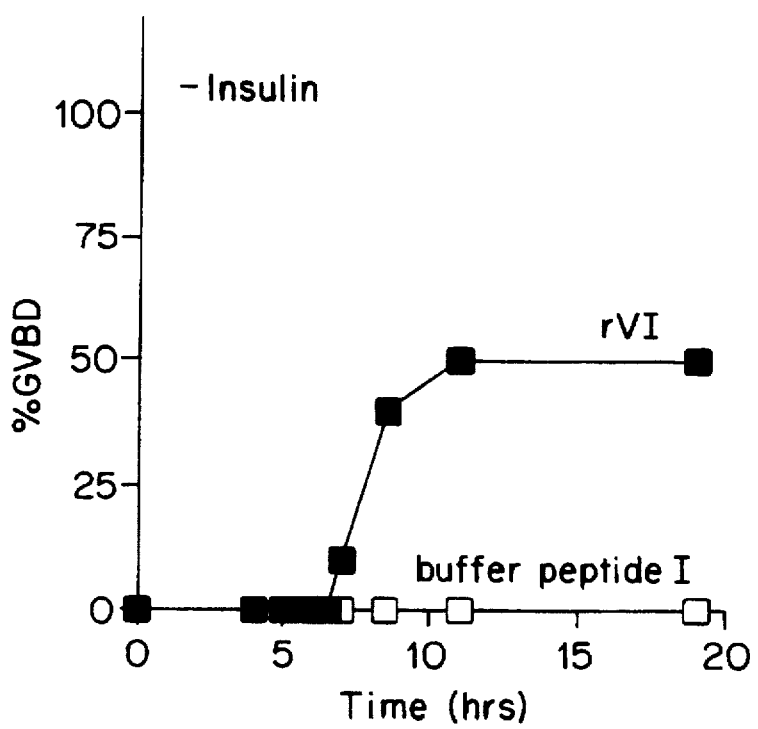

The oocyte maturation assay described above was also used to test the effect of various peptides derived from the PKC/RACK1 pair. Peptide I, derived from RACK1, as expected, inhibits the maturation of Xenopus oocytes presumably by interfering with the binding of βPKC1 to RACK1. On the other hand, a short peptide, rVI derived from the sixth WD-40 repeat in RACK1 enhances maturation. Ron, D., Mochly-Rosen, D., *J. Biol. Chem.* (1994) 269:21395–21398 This result is shown in FIG. 5. This peptide is believed to interfere with the RACK-mimicking site on PKC which normally covers the RACK-binding site in the absence of activation.

EXAMPLE 4

Figure 6:
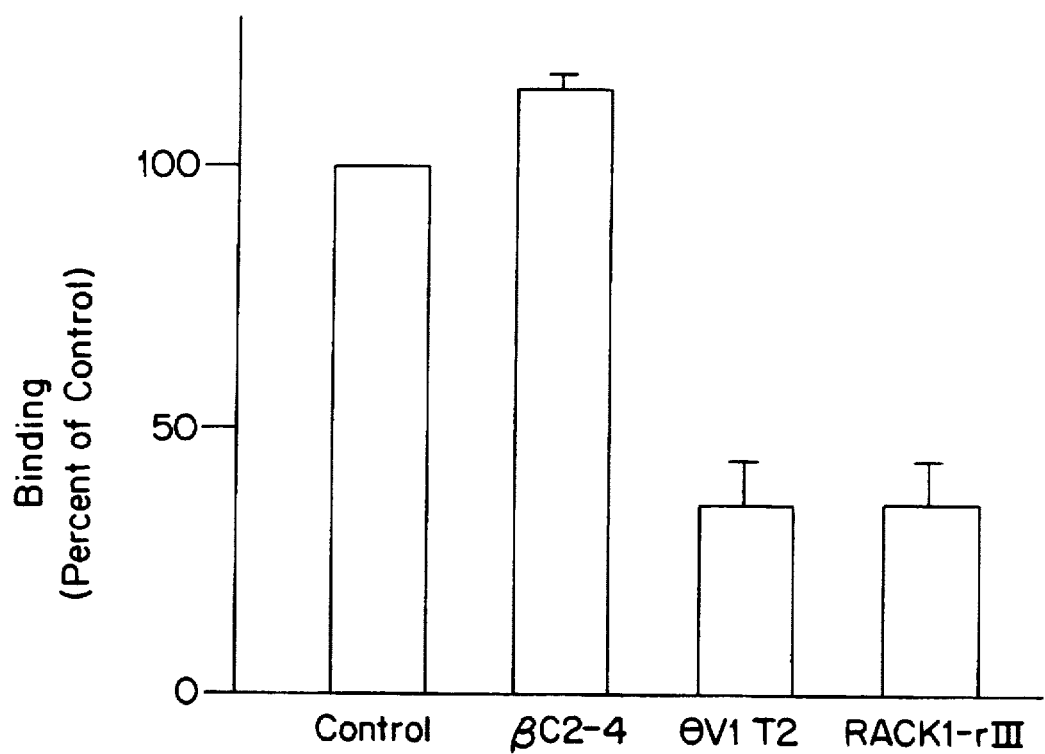
FIG. 6 shows the effect of various peptides on the binding of θPKC V1 fragment to RACK1 in vitro.

Interaction Peptides Derived from θPKC

θPKC is a member of the nPKC family and lacks a C2 region. Comparison of variable sequences of εPKC to other isozymes reveals regions of maximum disparity. Of these regions, some are strongly conserved across vast phylogenetic spans, e.g., from mammals to the invertebrate Aplysia. Isozyme specific sequences that are strongly conserved by evolution are probable sites for binding cognate proteins. Comparing δPKC to θPKC in the analogous region allowed identification of a θ-specific peptide expected to interfere with PKC binding to a RACK. Peptides with these characteristics from the V1 region of θPKC were prepared and tested for their ability to inhibit the binding of θPKC V1 fragment to RACK1 in vitro. The results are shown in FIG. 6. Of a multiplicity of peptides tested, both from other regions of the θPKC isoenzyme and from alternative isoenzymes in the family, only θV1 derived peptides θV1-1 and θV1-2, having the amino acid sequences GLSNFDCG (SEQ ID NO:9) (θPKC residues 8-15) and YVESENGQMYI (SEQ ID NO:10) (θPKC residues 36-46), respectively, were able to affect the interaction negatively. As expected, peptides rIII and rVI derived from the WD-40 regions of RACK1 were also effective.

Figure 7:
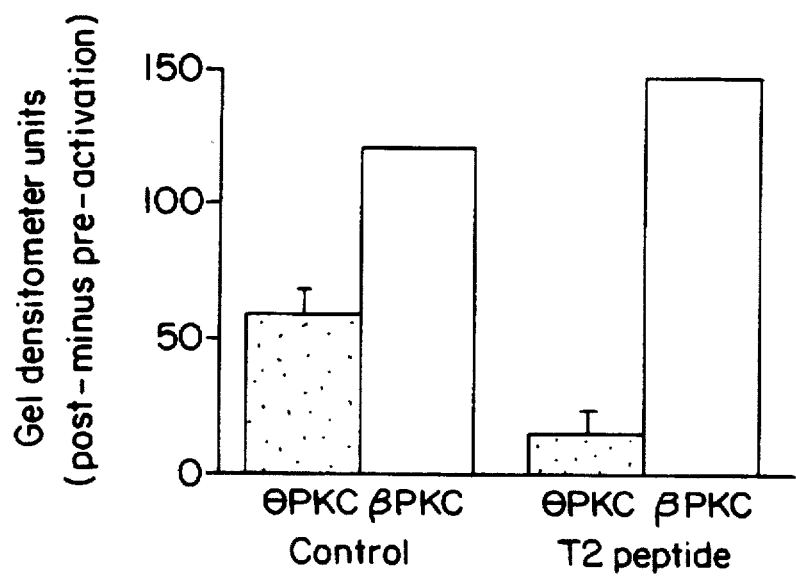
FIG. 7 shows the differential effects of the peptide T2 on translocation of θPKC V1 fragment and βPKC in intact cells.

The peptides θV1-1 and θV1-2 could inhibit the translocation of θPKC to the cellular particulate fraction in T-Jurkat cells. The specificity of this interaction is shown in FIG. 7 which shows inhibition by the θPKC V1 peptide (T2) of the translocation of θPKC but not of θPKC.

Sequences derived from other PKC regions.

V3 region. The V3 or hinge region separates the regulatory and catalytic domains. This region contains the sites of proteolysis by trypsin and calpain. The lack of conservation of the V3 domain between the different PKC isozymes suggests that this section may also be at least, in part, involved in targeting the PKC isozymes to their anchoring proteins. Furthermore, it has been demonstrated that regions within the V3 of αPKC mediate the translocation of that isozyme to the nucleus (James G., and Olson E. *J. Cell Biol.* 116:863–873, 1992). The V3 region of θPKC was found to bind to RACK1 in vitro. Therefore, the V3 region could affect not only the targeting of the activated isozymes (in which the V3-region is exposed) but could also regulate the enzyme susceptibilities to proteolysis.

V5. The amino acid sequences of the βPKC isoforms βIPKC and βIIPKC are identical except for variability within the V5 region (35 amino acids for βIPKC and 38 amino acids for βIIPKC). Upon activation, βIPKC and βIIPKC translocate to different localization sites in the cell (Disatnik M.-H., Buraggi G., Mochly-Rosen D. *Exp. Cell Res.* (1994) 210:287–297). This difference in localization of isozymes that are almost identical can be explained by the importance of the V5 region in mediating their targeting. Moreover, βIIPKC was found to selectively translocate to the nucleus upon proliferative stimulation where it selectively phosphorylated the nuclear envelope protein Iamin $B_1$. (Murray N. R. Burns D. J. Fields A. P. (1994) *J. Biol. Chem.* 269:21385–21390).

PKC-related proteins. Recently the human cDNAs encoding two novel protein kinases have been cloned. These proteins termed PRK1 and PRK2 (protein kinase C related kinase 1 and 2) show high homology to each other and some homology to the regulatory region of PKC (Palmer R. H., Ridden J., P. J. Parker *Eur. J. Biochem.* (1995) 227:344–351. Since the sequences within the regulatory domain of PKC are responsible for the interaction between a PKC and its anchoring proteins, sequences from PRK1 and PRK2 which show homology to functionally important sequences within the regulatory domain of PKC, are likely to be of biological importance.

Sequences from other isozymes and related proteins that meet the same isozyme selectivity/evolutionary conservation criteria include the following:

Peptides derived from the V1 region of PKC isozymes (Human):

| Peptide | Sequence | Position |
|---|---|---|
| θV1-1(SEQ ID NO:9) | G-L-S-N-F-D-C-G | θPKC(8–15) |
| θV1-2(SEQ ID NO:10) | Y-V-E-S-E-N-G-Q-M-Y-I | θPKC(36–46) |
| θV1-3(SEQ ID NO:11) | I-V-K-G-K-N-V-D-L-I | θPKC(73–82) |
| θV1-4(SEQ ID NO:12) | D-M-N-E-F-E-T-E-G-F | θPKC(130–139) |
| δV1-1(SEQ ID NO:13) | A-F-N-S-Y-E-L-G-S | δPKC(8–16) |
| δV1-2(SEQ ID NO:14) | A-L-S-T-E-R-G-K-T-L-V | δPKC(35–45) |
| δV1-3(SEQ ID NO:15) | V-L-M-R-A-A-E-E-P-V | δPKC(72–82) |
| δV1-4(SEQ ID NO:16) | Q-S-M-R-S-E-D-E-A-K | δPKC(129–138) |
| εV1-1(SEQ ID NO:17) | N-G-L-L-K-I-K | εPKC(5–11) |
| εV1-2(SEQ ID NO:2) | E-A-V-S-L-K-P-T | εPKC(14–21) |
| εV1-3(SEQ ID NO:18) | L-A-V-F-H-D-A-P-I-G-Y | εPKC(81–91) |
| εV1-4(SEQ ID NO:19) | D-D-F-V-A-N-C-T-I | εPKC(92–100) |
| εV1-5(SEQ ID NO:20) | W-I-D-L-E-P-E-G-R-V | εPKC(116–125) |
| εV1-6(SEQ ID NO:21) | H-A-V-G-P-R-P-Q-T-F | εPKC(27–36) |
| εV1-7(SEQ ID NO:22) | N-G-S-R-H-F-E-D | εPKC(108–115) |
| ηV1-1(SEQ ID NO:23) | N-G-Y-L-R-V-R | ηPKC(9–15) |
| ηV1-2(SEQ ID NO:24) | E-A-V-G-L-Q-P-T | ηPKC(18–25) |
| ηV1-3(SEQ ID NO:25) | L-A-V-F-H-E-T-P-L-G-Y | ηPKC(84–94) |
| ηV1-4(SEQ ID NO:26) | D-F-V-A-N-C-T-L | ηPKC(95–102) |
| ηV1-5(SEQ ID NO:27) | W-V-D-L-E-P-E-G-K-V | ηPKC(120–129) |
| ηV1-6(SEQ ID NO:28) | H-S-L-F-K-K-G-H | ηPKC(31–38) |
| ηV1-7(SEQ ID NO:29) | T-G-A-S-D-T-F-E-G | ηPKC(111–119) |
| μV1-1(SEQ ID NO:30) | M-S-V-P-P-L-L-R-P | μPKC(1–9) |
| μV1-2(SEQ ID NO:31) | K-F-P-E-C-G-F-Y-G-L-Y | μPKC(86–96) |
| λV1-1(SEQ ID NO:32) | H-Q-V-R-V-K-A-Y-Y-R | λPKC(15–24) |
| λV1-2(SEQ ID NO:33) | Y-E-L-N-K-D-S-E-L-L-I | λPKC(87–94) |
| ζV1-1(SEQ ID NO:34) | V-R-L-K-A-H-Y | ζPKC(16–22) |
| ζV1-2(SEQ ID NO:35) | V-D-S-E-G-D | ζPKC(61–66) |
| ζV1-3(SEQ ID NO:36) | V-F-P-S-I-P-E-Q | ζPKC(95–102) |

Peptides derived from the V3 region of PKC isozymes (Human):

| Peptide | Sequence | Position |
|---|---|---|
| δV3-1(SEQ ID NO:37) | Q-G-F-E-K-K-T-G-V | δPKC(312–320) |
| δV3-2(SEQ ID NO:38) | D-N-N-G-T-Y-G-K-I | δPKC(327–335) |
| εV3-1(SEQ ID NO:39) | S-S-P-S-E-E-D-R-S | εPKC(336–344) |
| εV3-2(SEQ ID NO:40) | P-C-D-Q-E-I-K-E | εPKC(351–358) |
| εV3-3(SEQ ID NO:41) | E-N-N-I-R-K-A-L-S | εPKC(360–368) |
| εV3-4(SEQ ID NO:42) | G-E-V-R-Q-G-Q-A | εPKC(393–400) |
| λV3-1(SEQ ID NO:43) | M-D-Q-S-S-M-H-S-D-H-A-Q-T-V-I | λPKC(194–208) |
| λV3-2(SEQ ID NO:44) | L-D-Q-V-G-E-E | λPKC(218–224) |
| λV3-3(SEQ ID NO:45) | E-A-M-N-T-R-E-S-G | λPKC(227–234) |
| μV3-1(SEQ ID NO:46) | D-P-D-A-D-Q-E-D-S | μPKC(390–398) |
| μV3-2(SEQ ID NO:47) | S-K-D-T-L-R-K-R-H | μPKC(440–448) |
| μV3-3(SEQ ID NO:48) | I-T-L-F-Q-N-D-T-G | μPKC(457–465) |
| μV3-4(SEQ ID NO:49) | G-S-N-S-H-K-D-I-S | μPKC(559–567) |
| θV3-1(SEQ ID NO:50) | C-S-I-K-N-E-A-R-L | θPKC(322–330) |
| θV3-2(SEQ ID NO:51) | G-K-R-E-P-Q-G-I-S | θPKC(337–345) |
| θV3-3(SEQ ID NO:52) | D-E-V-D-K-M-C-H-L | θPKC(351–359) |
| ζV3-1(SEQ ID NO:53) | S-Q-E-P-P-V-D-D-K-N-E-D-A-D-L | ζPKC(194–208) |
| ζV3-2(SEQ ID NO:54) | I-K-D-D-S-E-D | ζPKC(217–223) |
| ζV3-3(SEQ ID NO:55) | P-V-I-D-G-M-D-G-I | ζPKC(226–234) |
| βV3-1(SEQ ID NO:56) | V-P-P-E-G-S-E-A | βPKC(290–297) |
| αV3-1(SEQ ID NO:57) | I-P-E-G-D-E-E-G | αPKC(290–297) |
| γV3-1(SEQ ID NO:58) | V-A-D-A-D-N-C-S | γPKC(290–297) |

Peptides derived from the V5 region of PKC isozymes (Human):

| Peptide | Sequence | Position |
|---|---|---|
| αV5-1(SEQ ID NO:59) | Q-L-V-I-A-N | αPKC(642–647) |
| βIV5-1(SEQ ID NO:60) | K-L-F-I-M-N | βIPKC(646–651) |
| βIIV5-1(SEQ ID NO:61) | Q-E-V-I-R-N | βIIPKC(645–650) |
| δV5-1(SEQ ID NO:62) | K-N-L-I-D-S | δPKC(649–654) |
| εV5-1(SEQ ID NO:63) | E-A-I-V-K-Q | εPKC(714–719) |
| ηV5-1(SEQ ID NO:64) | E-G-H-L-P-M | ηPKC(657–662) |
| λV5-1(SEQ ID NO:65) | D-D-I-V-R-K | λPKC(559–564) |
| μV5-1(SEQ ID NO:66) | S-D-S-P-E-A | μPKC(898–903) |
| θV5-1(SEQ ID NO:67) | R-A-L-I-N-S | θPKC(680–685) |
| ζV5-1(SEQ ID NO:68) | E-D-A-I-K-R | ζPKC(556–561) |

Peptides derived deom protein kinase C related proteins (Human):

| Peptide | Sequence | Position |
|---|---|---|
| PRK1-1(SEQ ID NO:69) | Q-D-S-K-T-K-I-D | PRK1(171–178) |
| PRK2-1(SEQ ID NO:70) | Q-D-S-K-T-K-I-E | PRK2(181–188) |
| PRK1-2(SEQ ID NO:71) | E-L-A-V-F-W-R-D | PRK1(430–437) |
| PRK2-2(SEQ ID NO:72) | E-I-S-V-Y-W-R-D | PRK2(432–439) |
| PRK1-3(SEQ ID NO:73) | M-E-P-Q-G-C-L | PRK1(465–471) |
| PRK2-3(SEQ ID NO:74) | L-E-P-Q-G-T-L | PRK1(467–473) |

μV1-1, μV1-2 derived from μPKC were picked because they aligned with εV1-2 and θV1-2 and part of θV1-1 respectively. λV1-1 and λV1-2 from λPKC were picked based on their alignment with εV1-2 and part of εV1-3 and θV1-2 respectively. ζV1-1, ζV1-2, ζV1-3 derived from ζPKC were picked according to their homology to: εV1-2, θV1-2, and εV1-3 respectively. PRK1-1 and PRK2-2 were identified according to their homology to βC2-1. PRK1-2 and PRK2-2 were identified according to their homology to the biologically active εPKC-derived peptide εV1-3 and part of εV1-2. PRK1-3 and PRK2-3 were picked according to their alignment with the peptide εV1-5.

The peptide sequences were generated by aligning the human PKC sequences and the human PRK1 and PRK2 sequences using the MegAlign DNASTAR Inc. program. The sequences were aligned by using the clustal method. The algorithm groups sequences into clusters by examining the distances between all pairs. The clusters are aligned, first individually, then collectively to produce an overall alignment. (Higgins D. G. and Sharp, P. M. (1989). CABIOS, Vol 5, No 2, 151–153). The matrix for the alignment was PAM250 (percent accepted mutation 250–2.5 mutations per residue). This matrix allows only high stringency alignments.

We claim:

1. A method to ascertain a modulator of intracellular signal transduction mediated by the signal-generating protein, protein kinase C (PKC), from a library of candidate molecules, which method comprises providing the cognate receptor for activated kinase C (RACK) or a peptide derived from said PKC or the cognate RACK which binds specifically to the catalytically active PKC via a noncatalytic site of said PKC;

testing the candidate molecules of said library for the ability to modulate positively or negatively the binding of said cognate RACK or said peptide to the PKC in an assay not dependent on purity of the cognate RACK or PKC; and ascertaining as said modulator any candidate molecule that enhances or diminishes said binding.

2. The method of claim 1 wherein the testing is by a method which comprises contacting the PKC with the cognate RACK or peptide in the presence and absence of candidate molecule;

measuring the binding of the cognate RACK or peptide to PKC in the presence and absence of candidate molecules;

comparing the binding of cognate RACK or peptide to PKC in the presence and absence of candidate molecule; and identifying as a modulator a candidate molecule wherein the binding of the cognate RACK or peptide to the PKC is reduced or enhanced in the presence of said candidate molecule as compared to its absence.

3. The method of claim 2 wherein the binding is measured by measuring a metabolic effect.

4. The method of claim 3 wherein said metabolic effect is the maturation of a Xenopus oocyte, or induction of negative chronotropy in cardiac myocytes by an inducer, or transcription of a reporter gene, or subcellular translocation of a catalytically active signal-generating protein.

5. The method of claim 2 wherein the binding is measured by measuring a metabolic effect.

6. The method of claim 5 wherein said metabolic effect is subcellular translocation of catalytically active PKC.

7. The method of claim 2 wherein said peptide is derived from the PKC.

8. The method of claim 1 wherein said peptide is derived from the PKC.

9. The method of claim 8 wherein the peptide is selected from the group consisting of βC2-1, βC2-2, βC2-4, θV1-1, θV1-2, θV1-3, θV1-4, δV1-1, δV1-2, δV1-3, δV1-4, εV1-1, εV1-2, εV1-3, εV1-4, εV1-5, εV1-6, εV1-7, ηV1-1, ηV1-2, ηV1-3, ηV1-4, ηV1-5, ηV1-6, ηV1-7, μV1-1, μV1-2, λV1-1, λV1-2, ζV1-1, ζV1-2 and ζV1-3.

10. The method of claim 1 wherein said library of candidate molecules comprises peptides derived from the PKC or from the cognate RACK.

11. The method of claim 1 wherein said library of candidate molecules comprises nonpeptide molecules.

12. The peptide βC2-1, βC2-2, βC2-4, θV1-1, θV1-2, θV1-3, θV1-4, δV1-1, δV1-2, δV1-3, θV1-4, εV1-1, εV1-2, εV1-3, εV1-4, εV1-5, εV1-6, εV1-7, ηV1-1, ηV1-2, ηV1-3, ηV1-4, ηV1-5, ηV1-6, ηV1-7, μV1-1, μV1-2, λV1-1, λV1-2, ζV1-1, ζV1-2 or ζV1-3.

* * * * *

SEQUENCE LISTING ( 1 ) GENERAL INFORMATION:

( i i i ) NUMBER OF SEQUENCES: 74

( 2 ) INFORMATION FOR SEQ ID NO:1:

( i ) SEQUENCE CHARACTERISTICS:
    ( A ) LENGTH: 7 amino acids
    ( B ) TYPE: amino acid
    ( C ) STRANDEDNESS: single
    ( D ) TOPOLOGY: linear ( i i ) MOLECULE TYPE: peptide ( x i ) SEQUENCE DESCRIPTION: SEQ ID NO:1:

Asp  Tyr  Lys  Asp  Asp  Asp  Lys
  1                   5

( 2 ) INFORMATION FOR SEQ ID NO:2:

( i ) SEQUENCE CHARACTERISTICS:
    ( A ) LENGTH: 8 amino acids
    ( B ) TYPE: amino acid
    ( C ) STRANDEDNESS: single
    ( D ) TOPOLOGY: linear ( i i ) MOLECULE TYPE: peptide ( i x ) FEATURE:
    ( A ) NAME/KEY: Peptide
    ( B ) LOCATION: 1..8
    ( D ) OTHER INFORMATION: /label=epsilon-V1-2

( x i ) SEQUENCE DESCRIPTION: SEQ ID NO:2:

Glu  Ala  Val  Ser  Leu  Lys  Pro  Thr
  1                   5

( 2 ) INFORMATION FOR SEQ ID NO:3:

( i ) SEQUENCE CHARACTERISTICS:
    ( A ) LENGTH: 9 amino acids
    ( B ) TYPE: amino acid
    ( C ) STRANDEDNESS: single
    ( D ) TOPOLOGY: linear ( i i ) MOLECULE TYPE: peptide ( i x ) FEATURE:
    ( A ) NAME/KEY: Peptide
    ( B ) LOCATION: 1..9
    ( D ) OTHER INFORMATION: /label=beta-C2-4

( x i ) SEQUENCE DESCRIPTION: SEQ ID NO:3:

Ser  Leu  Asn  Pro  Glu  Trp  Asn  Glu  Thr
  1                   5

( 2 ) INFORMATION FOR SEQ ID NO:4:

( i ) SEQUENCE CHARACTERISTICS:
    ( A ) LENGTH: 8 amino acids
    ( B ) TYPE: amino acid
    ( C ) STRANDEDNESS: single
    ( D ) TOPOLOGY: linear ( i i ) MOLECULE TYPE: peptide ( i x ) FEATURE:
    ( A ) NAME/KEY: Peptide
    ( B ) LOCATION: 1..8
    ( D ) OTHER INFORMATION: /label=beta-C2-1

( x i ) SEQUENCE DESCRIPTION: SEQ ID NO:4:

Lys Gln Lys Thr Lys Thr Ile Lys
1               5

( 2 ) INFORMATION FOR SEQ ID NO:5:

( i ) SEQUENCE CHARACTERISTICS:
        ( A ) LENGTH: 13 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Peptide
        ( B ) LOCATION: 1..13
        ( D ) OTHER INFORMATION: /label=beta-C2-2

( x i ) SEQUENCE DESCRIPTION: SEQ ID NO:5:

Met Asp Pro Asn Gly Leu Ser Asp Pro Tyr Val Lys Leu
1               5                   10

( 2 ) INFORMATION FOR SEQ ID NO:6:

( i ) SEQUENCE CHARACTERISTICS:
        ( A ) LENGTH: 7 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Peptide
        ( B ) LOCATION: 1..7
        ( D ) OTHER INFORMATION: /label=beta-C2-3

( x i ) SEQUENCE DESCRIPTION: SEQ ID NO:6:

Ile Pro Asp Pro Lys Ser Glu
1               5

( 2 ) INFORMATION FOR SEQ ID NO:7:

( i ) SEQUENCE CHARACTERISTICS:
        ( A ) LENGTH: 8 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Peptide
        ( B ) LOCATION: 1..8
        ( D ) OTHER INFORMATION: /note= "Scrambled beta-C2-1"

( x i ) SEQUENCE DESCRIPTION: SEQ ID NO:7:

Thr Lys Gln Lys Lys Ile Thr Lys
1               5

( 2 ) INFORMATION FOR SEQ ID NO:8:

( i ) SEQUENCE CHARACTERISTICS:
        ( A ) LENGTH: 8 amino acids
        ( B ) TYPE: amino acid
        ( C ) STRANDEDNESS: single
        ( D ) TOPOLOGY: linear ( i i ) MOLECULE TYPE: peptide -continued (ix) FEATURE:
    (A) NAME/KEY: Peptide
    (B) LOCATION: 1..8
    (D) OTHER INFORMATION: /note= "Control Peptide"

(xi) SEQUENCE DESCRIPTION: SEQ ID NO:8:

```
Leu Gln Lys Ala Gly Val Asp Gly
1               5
```

(2) INFORMATION FOR SEQ ID NO:9:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Peptide
        (B) LOCATION: 1..8
        (D) OTHER INFORMATION: /label=theta-V1-1

(xi) SEQUENCE DESCRIPTION: SEQ ID NO:9:

```
Gly Leu Ser Asn Phe Asp Cys Gly
1               5
```

(2) INFORMATION FOR SEQ ID NO:10:

(i) SEQUENCE CHARACTERISTICS:
        (A) LENGTH: 11 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Peptide
        (B) LOCATION: 1..11
        (D) OTHER INFORMATION: /label=theta-V1-2

(xi) SEQUENCE DESCRIPTION: SEQ ID NO:10:

```
Tyr Val Glu Ser Glu Asn Gly Gln Met Tyr Ile
1               5                   10
```

(2) INFORMATION FOR SEQ ID NO:11:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Peptide
        (B) LOCATION: 1..10
        (D) OTHER INFORMATION: /label=theta-V1-3

(xi) SEQUENCE DESCRIPTION: SEQ ID NO:11:

```
Ile Val Lys Gly Lys Asn Val Asp Leu Ile
1               5                   10
```

(2) INFORMATION FOR SEQ ID NO:12:

(i) SEQUENCE CHARACTERISTICS:
        (A) LENGTH: 10 amino acids
        (B) TYPE: amino acid
        (C) STRANDEDNESS: single -continued ( D ) TOPOLOGY: linear ( i i ) MOLECULE TYPE: peptide ( i x ) FEATURE:
            ( A ) NAME/KEY: Peptide
            ( B ) LOCATION: 1..10
            ( D ) OTHER INFORMATION: /label=theta-V1-4

( x i ) SEQUENCE DESCRIPTION: SEQ ID NO:12:

Asp  Met  Asn  Glu  Phe  Glu  Thr  Glu  Gly  Phe
    1                   5                        10

( 2 ) INFORMATION FOR SEQ ID NO:13:

( i ) SEQUENCE CHARACTERISTICS:
            ( A ) LENGTH: 9 amino acids
            ( B ) TYPE: amino acid
            ( C ) STRANDEDNESS: single
            ( D ) TOPOLOGY: linear ( i i ) MOLECULE TYPE: peptide ( i x ) FEATURE:
            ( A ) NAME/KEY: Peptide
            ( B ) LOCATION: 1..9
            ( D ) OTHER INFORMATION: /label=delta-V1-1

( x i ) SEQUENCE DESCRIPTION: SEQ ID NO:13:

Ala  Phe  Asn  Ser  Tyr  Glu  Leu  Gly  Ser
    1                   5

( 2 ) INFORMATION FOR SEQ ID NO:14:

( i ) SEQUENCE CHARACTERISTICS:
            ( A ) LENGTH: 11 amino acids
            ( B ) TYPE: amino acid
            ( C ) STRANDEDNESS: single
            ( D ) TOPOLOGY: linear ( i i ) MOLECULE TYPE: peptide ( i x ) FEATURE:
            ( A ) NAME/KEY: Peptide
            ( B ) LOCATION: 1..11
            ( D ) OTHER INFORMATION: /label=delta-V1-2

( x i ) SEQUENCE DESCRIPTION: SEQ ID NO:14:

Ala  Leu  Ser  Thr  Glu  Arg  Gly  Lys  Thr  Leu  Val
    1                   5                        10

( 2 ) INFORMATION FOR SEQ ID NO:15:

( i ) SEQUENCE CHARACTERISTICS:
            ( A ) LENGTH: 10 amino acids
            ( B ) TYPE: amino acid
            ( C ) STRANDEDNESS: single
            ( D ) TOPOLOGY: linear ( i i ) MOLECULE TYPE: peptide ( i x ) FEATURE:
            ( A ) NAME/KEY: Peptide
            ( B ) LOCATION: 1..10
            ( D ) OTHER INFORMATION: /label=delta-V1-3

( x i ) SEQUENCE DESCRIPTION: SEQ ID NO:15:

Val  Leu  Met  Arg  Ala  Ala  Glu  Glu  Pro  Val
    1                   5                        10

( 2 ) INFORMATION FOR SEQ ID NO:16:

( i ) SEQUENCE CHARACTERISTICS:
  ( A ) LENGTH: 10 amino acids
  ( B ) TYPE: amino acid
  ( C ) STRANDEDNESS: single
  ( D ) TOPOLOGY: linear ( i i ) MOLECULE TYPE: peptide ( i x ) FEATURE:
  ( A ) NAME/KEY: Peptide
  ( B ) LOCATION: 1..10
  ( D ) OTHER INFORMATION: /label=delta-V1-4

( x i ) SEQUENCE DESCRIPTION: SEQ ID NO:16:

Gln Ser Met Arg Ser Glu Asp Glu Ala Lys
1               5                   10

( 2 ) INFORMATION FOR SEQ ID NO:17:

( i ) SEQUENCE CHARACTERISTICS:
    ( A ) LENGTH: 7 amino acids
    ( B ) TYPE: amino acid
    ( C ) STRANDEDNESS: single
    ( D ) TOPOLOGY: linear ( i i ) MOLECULE TYPE: peptide ( i x ) FEATURE:
    ( A ) NAME/KEY: Peptide
    ( B ) LOCATION: 1..7
    ( D ) OTHER INFORMATION: /label=epsilon-V1-1

( x i ) SEQUENCE DESCRIPTION: SEQ ID NO:17:

Asn Gly Leu Leu Lys Ile Lys
1               5

( 2 ) INFORMATION FOR SEQ ID NO:18:

( i ) SEQUENCE CHARACTERISTICS:
    ( A ) LENGTH: 11 amino acids
    ( B ) TYPE: amino acid
    ( C ) STRANDEDNESS: single
    ( D ) TOPOLOGY: linear ( i i ) MOLECULE TYPE: peptide ( i x ) FEATURE:
    ( A ) NAME/KEY: Peptide
    ( B ) LOCATION: 1..11
    ( D ) OTHER INFORMATION: /label=epsilon-V1-3

( x i ) SEQUENCE DESCRIPTION: SEQ ID NO:18:

Leu Ala Val Phe His Asp Ala Pro Ile Gly Tyr
1               5                   10

( 2 ) INFORMATION FOR SEQ ID NO:19:

( i ) SEQUENCE CHARACTERISTICS:
    ( A ) LENGTH: 9 amino acids
    ( B ) TYPE: amino acid
    ( C ) STRANDEDNESS: single
    ( D ) TOPOLOGY: linear ( i i ) MOLECULE TYPE: peptide ( i x ) FEATURE:
    ( A ) NAME/KEY: Peptide
    ( B ) LOCATION: 1..9
    ( D ) OTHER INFORMATION: /label=epsilon-V1-4

( x i ) SEQUENCE DESCRIPTION: SEQ ID NO:19:

Asp Asp Phe Val Ala Asn Cys Thr Ile
1               5

( 2 ) INFORMATION FOR SEQ ID NO:20:

( i ) SEQUENCE CHARACTERISTICS:
        ( A ) LENGTH: 10 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Peptide
        ( B ) LOCATION: 1..10
        ( D ) OTHER INFORMATION: /label=epsilon-V1-5

( x i ) SEQUENCE DESCRIPTION: SEQ ID NO:20:

```
Trp  Ile  Asp  Leu  Glu  Pro  Glu  Gly  Arg  Val
1                  5                        10
```

( 2 ) INFORMATION FOR SEQ ID NO:21:

( i ) SEQUENCE CHARACTERISTICS:
        ( A ) LENGTH: 10 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Peptide
        ( B ) LOCATION: 1..10
        ( D ) OTHER INFORMATION: /label=epsilon-V1-6

( x i ) SEQUENCE DESCRIPTION: SEQ ID NO:21:

```
His  Ala  Val  Gly  Pro  Arg  Pro  Gln  Thr  Phe
1                  5                        10
```

( 2 ) INFORMATION FOR SEQ ID NO:22:

( i ) SEQUENCE CHARACTERISTICS:
        ( A ) LENGTH: 8 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Peptide
        ( B ) LOCATION: 1..8
        ( D ) OTHER INFORMATION: /label=epsilon-V1-7

( x i ) SEQUENCE DESCRIPTION: SEQ ID NO:22:

```
Asn  Gly  Ser  Arg  His  Phe  Glu  Asp
1                  5
```

( 2 ) INFORMATION FOR SEQ ID NO:23:

( i ) SEQUENCE CHARACTERISTICS:
        ( A ) LENGTH: 7 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Peptide
        ( B ) LOCATION: 1..7
        ( D ) OTHER INFORMATION: /label= nu- V1-1

( x i ) SEQUENCE DESCRIPTION: SEQ ID NO:23:

Asn Gly Tyr Leu Arg Val Arg
1               5

( 2 ) INFORMATION FOR SEQ ID NO:24:

( i ) SEQUENCE CHARACTERISTICS:
        ( A ) LENGTH: 8 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Peptide
        ( B ) LOCATION: 1..8
        ( D ) OTHER INFORMATION: /label= nu- V1-2

( x i ) SEQUENCE DESCRIPTION: SEQ ID NO:24:

Glu Ala Val Gly Leu Gln Pro Thr
1               5

( 2 ) INFORMATION FOR SEQ ID NO:25:

( i ) SEQUENCE CHARACTERISTICS:
        ( A ) LENGTH: 11 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Peptide
        ( B ) LOCATION: 1..11
        ( D ) OTHER INFORMATION: /label= nu- V1-3

( x i ) SEQUENCE DESCRIPTION: SEQ ID NO:25:

Leu Ala Val Phe His Glu Thr Pro Leu Gly Tyr
1               5                   10

( 2 ) INFORMATION FOR SEQ ID NO:26:

( i ) SEQUENCE CHARACTERISTICS:
        ( A ) LENGTH: 8 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Peptide
        ( B ) LOCATION: 1..8
        ( D ) OTHER INFORMATION: /label= nu- V1-4

( x i ) SEQUENCE DESCRIPTION: SEQ ID NO:26:

Asp Phe Val Ala Asn Cys Thr Leu
1               5

( 2 ) INFORMATION FOR SEQ ID NO:27:

( i ) SEQUENCE CHARACTERISTICS:
        ( A ) LENGTH: 10 amino acids
        ( B ) TYPE: amino acid
        ( C ) STRANDEDNESS: single
        ( D ) TOPOLOGY: linear ( i i ) MOLECULE TYPE: peptide ( i x ) FEATURE:

```
            ( A ) NAME/KEY: Peptide
            ( B ) LOCATION: 1..10
            ( D ) OTHER INFORMATION: /label= nu- V1-5

( x i ) SEQUENCE DESCRIPTION: SEQ ID NO:27:

Trp  Val  Asp  Leu  Glu  Pro  Glu  Gly  Lys  Val
    1                   5                        10
```

( 2 ) INFORMATION FOR SEQ ID NO:28:

( i ) SEQUENCE CHARACTERISTICS:
        ( A ) LENGTH: 8 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Peptide
        ( B ) LOCATION: 1..8
        ( D ) OTHER INFORMATION: /label= nu- V1-6

( x i ) SEQUENCE DESCRIPTION: SEQ ID NO:28:

```
    His  Ser  Leu  Phe  Lys  Lys  Gly  His
    1                   5
```

( 2 ) INFORMATION FOR SEQ ID NO:29:

( i ) SEQUENCE CHARACTERISTICS:
        ( A ) LENGTH: 9 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Peptide
        ( B ) LOCATION: 1..9
        ( D ) OTHER INFORMATION: /label= nu- V1-7

( x i ) SEQUENCE DESCRIPTION: SEQ ID NO:29:

```
    Thr  Gly  Ala  Ser  Asp  Thr  Phe  Glu  Gly
    1                   5
```

( 2 ) INFORMATION FOR SEQ ID NO:30:

( i ) SEQUENCE CHARACTERISTICS:
        ( A ) LENGTH: 9 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Peptide
        ( B ) LOCATION: 1..9
        ( D ) OTHER INFORMATION: /label= mu- V1-1

( x i ) SEQUENCE DESCRIPTION: SEQ ID NO:30:

```
    Met  Ser  Val  Pro  Pro  Leu  Leu  Arg  Pro
    1                   5
```

( 2 ) INFORMATION FOR SEQ ID NO:31:

( i ) SEQUENCE CHARACTERISTICS:
        ( A ) LENGTH: 11 amino acids
        ( B ) TYPE: amino acid
        ( C ) STRANDEDNESS: single
        ( D ) TOPOLOGY: linear (  i  i  ) MOLECULE TYPE: peptide (  i x  ) FEATURE:
    ( A ) NAME/KEY: Peptide
    ( B ) LOCATION: 1..11
    ( D ) OTHER INFORMATION: /label= mu- V1-2

( x i ) SEQUENCE DESCRIPTION: SEQ ID NO:31:

```
Lys  Phe  Pro  Glu  Cys  Gly  Phe  Tyr  Gly  Leu  Tyr
 1                   5                        10
```

( 2 ) INFORMATION FOR SEQ ID NO:32:

( i ) SEQUENCE CHARACTERISTICS:
        ( A ) LENGTH: 10 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Peptide
        ( B ) LOCATION: 1..10
        ( D ) OTHER INFORMATION: /label=lambda-V1-1

( x i ) SEQUENCE DESCRIPTION: SEQ ID NO:32:

```
His  Gln  Val  Arg  Val  Lys  Ala  Tyr  Tyr  Arg
 1                   5                        10
```

( 2 ) INFORMATION FOR SEQ ID NO:33:

( i ) SEQUENCE CHARACTERISTICS:
        ( A ) LENGTH: 11 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Peptide
        ( B ) LOCATION: 1..11
        ( D ) OTHER INFORMATION: /label=lambda-V1-2

( x i ) SEQUENCE DESCRIPTION: SEQ ID NO:33:

```
Tyr  Glu  Leu  Asn  Lys  Asp  Ser  Glu  Leu  Leu  Ile
 1                   5                        10
```

( 2 ) INFORMATION FOR SEQ ID NO:34:

( i ) SEQUENCE CHARACTERISTICS:
        ( A ) LENGTH: 7 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Peptide
        ( B ) LOCATION: 1..7
        ( D ) OTHER INFORMATION: /label=zeta-V1-1

( x i ) SEQUENCE DESCRIPTION: SEQ ID NO:34:

```
Val  Arg  Leu  Lys  Ala  His  Tyr
 1                   5
```

( 2 ) INFORMATION FOR SEQ ID NO:35:

( i ) SEQUENCE CHARACTERISTICS:

(A) LENGTH: 6 amino acids
(B) TYPE: amino acid
(C) STRANDEDNESS: single
(D) TOPOLOGY: linear (ii) MOLECULE TYPE: peptide (ix) FEATURE:
(A) NAME/KEY: Peptide
(B) LOCATION: 1..6
(D) OTHER INFORMATION: /label=zeta-V1-2

(xi) SEQUENCE DESCRIPTION: SEQ ID NO:35:

Val Asp Ser Glu Gly Asp
1               5

(2) INFORMATION FOR SEQ ID NO:36:

(i) SEQUENCE CHARACTERISTICS:
(A) LENGTH: 8 amino acids
(B) TYPE: amino acid
(C) STRANDEDNESS: single
(D) TOPOLOGY: linear (ii) MOLECULE TYPE: peptide (ix) FEATURE:
(A) NAME/KEY: Peptide
(B) LOCATION: 1..8
(D) OTHER INFORMATION: /label=zeta-V1-3

(xi) SEQUENCE DESCRIPTION: SEQ ID NO:36:

Val Phe Pro Ser Ile Pro Glu Gln
1               5

(2) INFORMATION FOR SEQ ID NO:37:

(i) SEQUENCE CHARACTERISTICS:
(A) LENGTH: 9 amino acids
(B) TYPE: amino acid
(C) STRANDEDNESS: single
(D) TOPOLOGY: linear (ii) MOLECULE TYPE: peptide (ix) FEATURE:
(A) NAME/KEY: Peptide
(B) LOCATION: 1..9
(D) OTHER INFORMATION: /label=delta-V3-1

(xi) SEQUENCE DESCRIPTION: SEQ ID NO:37:

Gln Gly Phe Glu Lys Lys Thr Gly Val
1               5

(2) INFORMATION FOR SEQ ID NO:38:

(i) SEQUENCE CHARACTERISTICS:
(A) LENGTH: 9 amino acids
(B) TYPE: amino acid
(C) STRANDEDNESS: single
(D) TOPOLOGY: linear (ii) MOLECULE TYPE: peptide (ix) FEATURE:
(A) NAME/KEY: Peptide
(B) LOCATION: 1..9
(D) OTHER INFORMATION: /label=delta-V3-2

(xi) SEQUENCE DESCRIPTION: SEQ ID NO:38:

Asp Asn Asn Gly Thr Tyr Gly Lys Ile
1               5

(2) INFORMATION FOR SEQ ID NO:39:

(i) SEQUENCE CHARACTERISTICS:
(A) LENGTH: 9 amino acids
(B) TYPE: amino acid
(C) STRANDEDNESS: single
(D) TOPOLOGY: linear (ii) MOLECULE TYPE: peptide (ix) FEATURE:
(A) NAME/KEY: Peptide
(B) LOCATION: 1..9
(D) OTHER INFORMATION: /label=epsilon-V3-1

(xi) SEQUENCE DESCRIPTION: SEQ ID NO:39:

Ser Ser Pro Ser Glu Glu Asp Arg Ser
1               5

(2) INFORMATION FOR SEQ ID NO:40:

(i) SEQUENCE CHARACTERISTICS:
(A) LENGTH: 8 amino acids
(B) TYPE: amino acid
(C) STRANDEDNESS: single
(D) TOPOLOGY: linear (ii) MOLECULE TYPE: peptide (ix) FEATURE:
(A) NAME/KEY: Peptide
(B) LOCATION: 1..8
(D) OTHER INFORMATION: /label=epsilon-V3-2

(xi) SEQUENCE DESCRIPTION: SEQ ID NO:40:

Pro Cys Asp Gln Glu Ile Lys Glu
1               5

(2) INFORMATION FOR SEQ ID NO:41:

(i) SEQUENCE CHARACTERISTICS:
(A) LENGTH: 9 amino acids
(B) TYPE: amino acid
(C) STRANDEDNESS: single
(D) TOPOLOGY: linear (ii) MOLECULE TYPE: peptide (ix) FEATURE:
(A) NAME/KEY: Peptide
(B) LOCATION: 1..9
(D) OTHER INFORMATION: /label=epsilon-V3-3

(xi) SEQUENCE DESCRIPTION: SEQ ID NO:41:

Glu Asn Asn Ile Arg Lys Ala Leu Ser
1               5

(2) INFORMATION FOR SEQ ID NO:42:

(i) SEQUENCE CHARACTERISTICS:
(A) LENGTH: 8 amino acids
(B) TYPE: amino acid
(C) STRANDEDNESS: single
(D) TOPOLOGY: linear (ii) MOLECULE TYPE: peptide (ix) FEATURE:
(A) NAME/KEY: Peptide
(B) LOCATION: 1..8
(D) OTHER INFORMATION: /label=epsilon-V3-4

(xi) SEQUENCE DESCRIPTION: SEQ ID NO:42:

Gly Glu Val Arg Gln Gly Gln Ala
1               5

( 2 ) INFORMATION FOR SEQ ID NO:43:

( i ) SEQUENCE CHARACTERISTICS:
         ( A ) LENGTH: 15 amino acids
         ( B ) TYPE: amino acid
         ( C ) STRANDEDNESS: single
         ( D ) TOPOLOGY: linear ( i i ) MOLECULE TYPE: peptide ( i x ) FEATURE:
         ( A ) NAME/KEY: Peptide
         ( B ) LOCATION: 1..15
         ( D ) OTHER INFORMATION: /label=lambda-V3-1

( x i ) SEQUENCE DESCRIPTION: SEQ ID NO:43:

Met Asp Gln Ser Ser Met His Ser Asp His Ala Gln Thr Val Ile
1               5                   10                  15

( 2 ) INFORMATION FOR SEQ ID NO:44:

( i ) SEQUENCE CHARACTERISTICS:
         ( A ) LENGTH: 7 amino acids
         ( B ) TYPE: amino acid
         ( C ) STRANDEDNESS: single
         ( D ) TOPOLOGY: linear ( i i ) MOLECULE TYPE: peptide ( i x ) FEATURE:
         ( A ) NAME/KEY: Peptide
         ( B ) LOCATION: 1..7
         ( D ) OTHER INFORMATION: /label=lambda-V3-2

( x i ) SEQUENCE DESCRIPTION: SEQ ID NO:44:

Leu Asp Gln Val Gly Glu Glu
1               5

( 2 ) INFORMATION FOR SEQ ID NO:45:

( i ) SEQUENCE CHARACTERISTICS:
         ( A ) LENGTH: 9 amino acids
         ( B ) TYPE: amino acid
         ( C ) STRANDEDNESS: single
         ( D ) TOPOLOGY: linear ( i i ) MOLECULE TYPE: peptide ( i x ) FEATURE:
         ( A ) NAME/KEY: Peptide
         ( B ) LOCATION: 1..9
         ( D ) OTHER INFORMATION: /label=lambda-V3-3

( x i ) SEQUENCE DESCRIPTION: SEQ ID NO:45:

Glu Ala Met Asn Thr Arg Glu Ser Gly
1               5

( 2 ) INFORMATION FOR SEQ ID NO:46:

( i ) SEQUENCE CHARACTERISTICS:
         ( A ) LENGTH: 9 amino acids
         ( B ) TYPE: amino acid
         ( C ) STRANDEDNESS: single
         ( D ) TOPOLOGY: linear ( i i ) MOLECULE TYPE: peptide ( i x ) FEATURE:
         ( A ) NAME/KEY: Peptide ( B ) LOCATION: 1..9
( D ) OTHER INFORMATION: /label= mu- V3-1

( x i ) SEQUENCE DESCRIPTION: SEQ ID NO:46:

Asp Pro Asp Ala Asp Gln Glu Asp Ser
1               5

( 2 ) INFORMATION FOR SEQ ID NO:47:

( i ) SEQUENCE CHARACTERISTICS:
        ( A ) LENGTH: 9 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Peptide
        ( B ) LOCATION: 1..9
        ( D ) OTHER INFORMATION: /label= mu- V3-2

( x i ) SEQUENCE DESCRIPTION: SEQ ID NO:47:

Ser Lys Asp Thr Leu Arg Lys Arg His
1               5

( 2 ) INFORMATION FOR SEQ ID NO:48:

( i ) SEQUENCE CHARACTERISTICS:
        ( A ) LENGTH: 9 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Peptide
        ( B ) LOCATION: 1..9
        ( D ) OTHER INFORMATION: /label= mu- V3-3

( x i ) SEQUENCE DESCRIPTION: SEQ ID NO:48:

Ile Thr Leu Phe Gln Asn Asp Thr Gly
1               5

( 2 ) INFORMATION FOR SEQ ID NO:49:

( i ) SEQUENCE CHARACTERISTICS:
        ( A ) LENGTH: 9 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Peptide
        ( B ) LOCATION: 1..9
        ( D ) OTHER INFORMATION: /label= mu- V3-4

( x i ) SEQUENCE DESCRIPTION: SEQ ID NO:49:

Gly Ser Asn Ser His Lys Asp Ile Ser
1               5

( 2 ) INFORMATION FOR SEQ ID NO:50:

( i ) SEQUENCE CHARACTERISTICS:
        ( A ) LENGTH: 9 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
    ( A ) NAME/KEY: Peptide
    ( B ) LOCATION: 1..9
    ( D ) OTHER INFORMATION: /label=theta-V3-1

( x i ) SEQUENCE DESCRIPTION: SEQ ID NO:50:

Cys Ser Ile Lys Asn Glu Ala Arg Leu
1               5

( 2 ) INFORMATION FOR SEQ ID NO:51:

( i ) SEQUENCE CHARACTERISTICS:
        ( A ) LENGTH: 9 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Peptide
        ( B ) LOCATION: 1..9
        ( D ) OTHER INFORMATION: /label=theta-V3-2

( x i ) SEQUENCE DESCRIPTION: SEQ ID NO:51:

Gly Lys Arg Glu Pro Gln Gly Ile Ser
1               5

( 2 ) INFORMATION FOR SEQ ID NO:52:

( i ) SEQUENCE CHARACTERISTICS:
        ( A ) LENGTH: 9 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Peptide
        ( B ) LOCATION: 1..9
        ( D ) OTHER INFORMATION: /label=theta-V3-3

( x i ) SEQUENCE DESCRIPTION: SEQ ID NO:52:

Asp Glu Val Asp Lys Met Cys His Leu
1               5

( 2 ) INFORMATION FOR SEQ ID NO:53:

( i ) SEQUENCE CHARACTERISTICS:
        ( A ) LENGTH: 15 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Peptide
        ( B ) LOCATION: 1..15
        ( D ) OTHER INFORMATION: /label=zeta-V3-1

( x i ) SEQUENCE DESCRIPTION: SEQ ID NO:53:

Ser Gln Glu Pro Pro Val Asp Asp Lys Asn Glu Asp Ala Asp Leu
1               5                   10                  15

( 2 ) INFORMATION FOR SEQ ID NO:54:

( i ) SEQUENCE CHARACTERISTICS:
        ( A ) LENGTH: 7 amino acids ( B ) TYPE: amino acid
( C ) STRANDEDNESS: single
( D ) TOPOLOGY: linear ( i i ) MOLECULE TYPE: peptide ( i x ) FEATURE:
( A ) NAME/KEY: Peptide
( B ) LOCATION: 1..7
( D ) OTHER INFORMATION: /label=zeta-V3-2

( x i ) SEQUENCE DESCRIPTION: SEQ ID NO:54:

Ile Lys Asp Asp Ser Glu Asp
1               5

( 2 ) INFORMATION FOR SEQ ID NO:55:

( i ) SEQUENCE CHARACTERISTICS:
( A ) LENGTH: 9 amino acids
( B ) TYPE: amino acid
( C ) STRANDEDNESS: single
( D ) TOPOLOGY: linear ( i i ) MOLECULE TYPE: peptide ( i x ) FEATURE:
( A ) NAME/KEY: Peptide
( B ) LOCATION: 1..9
( D ) OTHER INFORMATION: /label=zeta-V3-3

( x i ) SEQUENCE DESCRIPTION: SEQ ID NO:55:

Pro Val Ile Asp Gly Met Asp Gly Ile
1               5

( 2 ) INFORMATION FOR SEQ ID NO:56:

( i ) SEQUENCE CHARACTERISTICS:
( A ) LENGTH: 8 amino acids
( B ) TYPE: amino acid
( C ) STRANDEDNESS: single
( D ) TOPOLOGY: linear ( i i ) MOLECULE TYPE: peptide ( i x ) FEATURE:
( A ) NAME/KEY: Peptide
( B ) LOCATION: 1..8
( D ) OTHER INFORMATION: /label=beta-V3-1

( x i ) SEQUENCE DESCRIPTION: SEQ ID NO:56:

Val Pro Pro Glu Gly Ser Glu Ala
1               5

( 2 ) INFORMATION FOR SEQ ID NO:57:

( i ) SEQUENCE CHARACTERISTICS:
( A ) LENGTH: 8 amino acids
( B ) TYPE: amino acid
( C ) STRANDEDNESS: single
( D ) TOPOLOGY: linear ( i i ) MOLECULE TYPE: peptide ( i x ) FEATURE:
( A ) NAME/KEY: Peptide
( B ) LOCATION: 1..8
( D ) OTHER INFORMATION: /label=alpha-V3-1

( x i ) SEQUENCE DESCRIPTION: SEQ ID NO:57:

Ile Pro Glu Gly Asp Glu Glu Gly
1               5

( 2 ) INFORMATION FOR SEQ ID NO:58:

( i ) SEQUENCE CHARACTERISTICS:
        ( A ) LENGTH: 8 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Peptide
        ( B ) LOCATION: 1..8
        ( D ) OTHER INFORMATION: /label=gamma-V3-1

( x i ) SEQUENCE DESCRIPTION: SEQ ID NO:58:

Val Ala Asp Ala Asp Asn Cys Ser
    1                 5

( 2 ) INFORMATION FOR SEQ ID NO:59:

( i ) SEQUENCE CHARACTERISTICS:
        ( A ) LENGTH: 6 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Peptide
        ( B ) LOCATION: 1..6
        ( D ) OTHER INFORMATION: /label=alpha-V5-1

( x i ) SEQUENCE DESCRIPTION: SEQ ID NO:59:

Gln Leu Val Ile Ala Asn
    1              5

( 2 ) INFORMATION FOR SEQ ID NO:60:

( i ) SEQUENCE CHARACTERISTICS:
        ( A ) LENGTH: 6 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Peptide
        ( B ) LOCATION: 1..6
        ( D ) OTHER INFORMATION: /label=beta-I-V5-1

( x i ) SEQUENCE DESCRIPTION: SEQ ID NO:60:

Lys Leu Phe Ile Met Asn
    1              5

( 2 ) INFORMATION FOR SEQ ID NO:61:

( i ) SEQUENCE CHARACTERISTICS:
        ( A ) LENGTH: 6 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Peptide
        ( B ) LOCATION: 1..6
        ( D ) OTHER INFORMATION: /label=beta-II-V5-1

( x i ) SEQUENCE DESCRIPTION: SEQ ID NO:61:

```
        Gln Glu Val Ile Arg Asn
        1               5
```

( 2 ) INFORMATION FOR SEQ ID NO:62:

( i ) SEQUENCE CHARACTERISTICS:
    ( A ) LENGTH: 6 amino acids
    ( B ) TYPE: amino acid
    ( C ) STRANDEDNESS: single
    ( D ) TOPOLOGY: linear ( i i ) MOLECULE TYPE: peptide ( i x ) FEATURE:
    ( A ) NAME/KEY: Peptide
    ( B ) LOCATION: 1..6
    ( D ) OTHER INFORMATION: /label=delta-V5-1

( x i ) SEQUENCE DESCRIPTION: SEQ ID NO:62:

```
        Lys Asn Leu Ile Asp Ser
        1               5
```

( 2 ) INFORMATION FOR SEQ ID NO:63:

( i ) SEQUENCE CHARACTERISTICS:
    ( A ) LENGTH: 6 amino acids
    ( B ) TYPE: amino acid
    ( C ) STRANDEDNESS: single
    ( D ) TOPOLOGY: linear ( i i ) MOLECULE TYPE: peptide ( i x ) FEATURE:
    ( A ) NAME/KEY: Peptide
    ( B ) LOCATION: 1..6
    ( D ) OTHER INFORMATION: /label=epsilon-V5-1

( x i ) SEQUENCE DESCRIPTION: SEQ ID NO:63:

```
        Glu Ala Ile Val Lys Gln
        1               5
```

( 2 ) INFORMATION FOR SEQ ID NO:64:

( i ) SEQUENCE CHARACTERISTICS:
    ( A ) LENGTH: 6 amino acids
    ( B ) TYPE: amino acid
    ( C ) STRANDEDNESS: single
    ( D ) TOPOLOGY: linear ( i i ) MOLECULE TYPE: peptide ( i x ) FEATURE:
    ( A ) NAME/KEY: Peptide
    ( B ) LOCATION: 1..6
    ( D ) OTHER INFORMATION: /label= nu- V5-1

( x i ) SEQUENCE DESCRIPTION: SEQ ID NO:64:

```
        Glu Gly His Leu Pro Met
        1               5
```

( 2 ) INFORMATION FOR SEQ ID NO:65:

( i ) SEQUENCE CHARACTERISTICS:
    ( A ) LENGTH: 6 amino acids
    ( B ) TYPE: amino acid
    ( C ) STRANDEDNESS: single
    ( D ) TOPOLOGY: linear ( i i ) MOLECULE TYPE: peptide ( i x ) FEATURE:
    ( A ) NAME/KEY: Peptide
    ( B ) LOCATION: 1..6

(D) OTHER INFORMATION: /label=lambda-V5-1

(x i) SEQUENCE DESCRIPTION: SEQ ID NO:65:

Asp Asp Ile Val Arg Lys
1               5

(2) INFORMATION FOR SEQ ID NO:66:

(i) SEQUENCE CHARACTERISTICS:
        (A) LENGTH: 6 amino acids
        (B) TYPE: amino acid
        (C) STRANDEDNESS: single
        (D) TOPOLOGY: linear (i i) MOLECULE TYPE: peptide (i x) FEATURE:
        (A) NAME/KEY: Peptide
        (B) LOCATION: 1..6
        (D) OTHER INFORMATION: /label= mu- V5-1

(x i) SEQUENCE DESCRIPTION: SEQ ID NO:66:

Ser Asp Ser Pro Glu Ala
1               5

(2) INFORMATION FOR SEQ ID NO:67:

(i) SEQUENCE CHARACTERISTICS:
        (A) LENGTH: 6 amino acids
        (B) TYPE: amino acid
        (C) STRANDEDNESS: single
        (D) TOPOLOGY: linear (i i) MOLECULE TYPE: peptide (i x) FEATURE:
        (A) NAME/KEY: Peptide
        (B) LOCATION: 1..6
        (D) OTHER INFORMATION: /label=theta-V5-1

(x i) SEQUENCE DESCRIPTION: SEQ ID NO:67:

Arg Ala Leu Ile Asn Ser
1               5

(2) INFORMATION FOR SEQ ID NO:68:

(i) SEQUENCE CHARACTERISTICS:
        (A) LENGTH: 6 amino acids
        (B) TYPE: amino acid
        (C) STRANDEDNESS: single
        (D) TOPOLOGY: linear (i i) MOLECULE TYPE: peptide (i x) FEATURE:
        (A) NAME/KEY: Peptide
        (B) LOCATION: 1..6
        (D) OTHER INFORMATION: /label=zeta-V5-1

(x i) SEQUENCE DESCRIPTION: SEQ ID NO:68:

Glu Asp Ala Ile Lys Arg
1               5

(2) INFORMATION FOR SEQ ID NO:69:

(i) SEQUENCE CHARACTERISTICS:
        (A) LENGTH: 8 amino acids
        (B) TYPE: amino acid
        (C) STRANDEDNESS: single
        (D) TOPOLOGY: linear (i i) MOLECULE TYPE: peptide ( i x ) FEATURE:
        ( A ) NAME/KEY: Peptide
        ( B ) LOCATION: 1..8
        ( D ) OTHER INFORMATION: /label=PRK1-1

( x i ) SEQUENCE DESCRIPTION: SEQ ID NO:69:

```
Gln Asp Ser Lys Thr Lys Ile Asp
1               5
```

( 2 ) INFORMATION FOR SEQ ID NO:70:

( i ) SEQUENCE CHARACTERISTICS:
        ( A ) LENGTH: 8 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Peptide
        ( B ) LOCATION: 1..8
        ( D ) OTHER INFORMATION: /label=PRK2-1

( x i ) SEQUENCE DESCRIPTION: SEQ ID NO:70:

```
Gln Asp Ser Lys Thr Lys Ile Glu
1               5
```

( 2 ) INFORMATION FOR SEQ ID NO:71:

( i ) SEQUENCE CHARACTERISTICS:
        ( A ) LENGTH: 8 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Peptide
        ( B ) LOCATION: 1..8
        ( D ) OTHER INFORMATION: /label=PRK1-2

( x i ) SEQUENCE DESCRIPTION: SEQ ID NO:71:

```
Glu Leu Ala Val Phe Trp Arg Asp
1               5
```

( 2 ) INFORMATION FOR SEQ ID NO:72:

( i ) SEQUENCE CHARACTERISTICS:
        ( A ) LENGTH: 8 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Peptide
        ( B ) LOCATION: 1..8
        ( D ) OTHER INFORMATION: /label=PRK2-2

( x i ) SEQUENCE DESCRIPTION: SEQ ID NO:72:

```
Glu Ile Ser Val Tyr Trp Arg Asp
1               5
```

( 2 ) INFORMATION FOR SEQ ID NO:73:

( i ) SEQUENCE CHARACTERISTICS:
        ( A ) LENGTH: 7 amino acids
        ( B ) TYPE: amino acid

```
            ( C ) STRANDEDNESS: single
            ( D ) TOPOLOGY: linear ( i i ) MOLECULE TYPE: peptide ( i x ) FEATURE:
            ( A ) NAME/KEY: Peptide
            ( B ) LOCATION: 1..7
            ( D ) OTHER INFORMATION: /label=PRK1-3

( x i ) SEQUENCE DESCRIPTION: SEQ ID NO:73:

Met  Glu  Pro  Gln  Gly  Cys  Leu
    1                    5

( 2 ) INFORMATION FOR SEQ ID NO:74:

( i ) SEQUENCE CHARACTERISTICS:
            ( A ) LENGTH: 7 amino acids
            ( B ) TYPE: amino acid
            ( C ) STRANDEDNESS: single
            ( D ) TOPOLOGY: linear ( i i ) MOLECULE TYPE: peptide ( i x ) FEATURE:
            ( A ) NAME/KEY: Peptide
            ( B ) LOCATION: 1..7
            ( D ) OTHER INFORMATION: /label=PRK2-3

( x i ) SEQUENCE DESCRIPTION: SEQ ID NO:74:

Leu  Glu  Pro  Gln  Gly  Thr  Leu
    1                    5
```